United States Patent
Acton, III et al.

(10) Patent No.: US 7,393,960 B2
(45) Date of Patent: Jul. 1, 2008

(54) INDOLES HAVING ANTI-DIABETIC ACTIVITY

(75) Inventors: John J. Acton, III, Cranford, NJ (US); Peter T. Meinke, Plainfield, NJ (US); Harold B. Wood, Westfield, NJ (US); Regina M. Black, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 388 days.

(21) Appl. No.: 10/525,470

(22) PCT Filed: Aug. 28, 2003

(86) PCT No.: PCT/US03/26679

§ 371 (c)(1), (2), (4) Date: Feb. 24, 2005

(87) PCT Pub. No.: WO2004/019869

PCT Pub. Date: Mar. 11, 2004

(65) Prior Publication Data

US 2005/0272788 A1    Dec. 8, 2005

Related U.S. Application Data

(60) Provisional application No. 60/440,741, filed on Jan. 17, 2003, provisional application No. 60/406,737, filed on Aug. 29, 2002.

(51) Int. Cl.
   *C07D 261/20* (2006.01)
   *A01N 43/80* (2006.01)

(52) U.S. Cl. ............................ 548/241; 514/379

(58) Field of Classification Search .............. None
   See application file for complete search history.

(56) References Cited

U.S. PATENT DOCUMENTS

| 5,482,960 | A | 1/1996 | Berryman et al. |
| 5,686,481 | A | 11/1997 | Elliott et al. |
| 6,372,742 | B1 * | 4/2002 | Chin et al. ............... 514/236.8 |
| 7,186,746 | B2 * | 3/2007 | Acton et al. ................ 514/419 |

FOREIGN PATENT DOCUMENTS

| EP | 1 424 325 | 2/2001 |
| WO | WO 98 08818 | 3/1998 |
| WO | WO 99 43651 | 9/1999 |
| WO | WO 99 43654 | 9/1999 |
| WO | WO 99 43672 | 9/1999 |
| WO | WO 01 30343 | 5/2001 |
| WO | WO 02 08188 | 1/2002 |
| WO | WO 02 30895 | 4/2002 |
| WO | WO 2004 006920 | 1/2004 |

OTHER PUBLICATIONS

Liu et al., "Selective PPARg modulators with improved pharmacological profiles", Bioorg. Med. Chem. Lett., 15, 2005, 2437-2440.*

* cited by examiner

*Primary Examiner*—Joseph McKane
*Assistant Examiner*—Sun Jae Y Loewe
(74) *Attorney, Agent, or Firm*—Richard C. Billups; James L. McGinnis; Catherine D. Fitch

(57) ABSTRACT

Indoles having aryloxyalkanoic acid substituents or arylalkanoic acid substituents are agonists or partial agonists of PPAR gamma and are useful in the treatment and control of hyperglycemia that is symptomatic of type II diabetes, as well as dyslipidemia, hyperlipidemia, hypercholesterolemia, hypertriglyceridemia, and obesity that are often associated with type 2 diabetes.

17 Claims, No Drawings

INDOLES HAVING ANTI-DIABETIC ACTIVITY

CROSS REFERENCE TO RELATED APPLICATIONS

This application is a U.S. National Phase application under 35 U.S.C. § 371 of PCT Application No. PCT/US03/26679, filed Aug. 28, 2003, and claims priority under 35 U.S.C. § 119 (e) from U.S. application Ser. No. 60/406,737 filed Aug. 29, 2002, and U.S. Application No. 60/440,741 filed Jan. 17, 2003.

FIELD OF THE INVENTION

The instant invention is concerned with indoles having an aryloxyalkanoic acid substituent, and pharmaceutically acceptable salts and prodrugs thereof, which are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients are insulin resistant, which means that they have a resistance to the effect of insulin in stimulating glucose and lipid metabolism in the main insulin-sensitive tissues, which are muscle, liver and adipose tissues. Patients who are insulin resistant but not diabetic compensate for the insulin resistance by secreting more insulin, so that serum glucose levels are not elevated enough to meet the criteria of Type 2 diabetes. In patients with Type 2 diabetes, even elevated plasma insulin levels are insufficient to overcome the pronounced insulin resistance.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance or Type 2 diabetes often have several symptoms that together are referred to as syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Insulin resistance is not primarily caused by a diminished number of insulin receptors but by a post-insulin receptor binding defect that is not yet completely understood. This lack of responsiveness to insulin results in insufficient insulin-mediated activation of uptake, oxidation and storage of glucose in muscle and inadequate insulin-mediated repression of lipolysis in adipose tissue and of glucose production and secretion in the liver.

There are several available treatments for type 2 diabetes, each of which has its own limitations and potential risks. Physical exercise and a reduction in dietary intake of calories often dramatically improve the diabetic condition and are the best first line treatment of type 2 diabetes. Compliance with this treatment is very poor because of well-entrenched sedentary lifestyles and excess food consumption, especially of foods containing high amounts of fat. A widely used drug treatment involves the administration of meglitinide or a sulfonylurea (e.g. tolbutamide or glipizide), which are insulin secretagogues. These drugs increase the plasma level of insulin by stimulating the pancreatic β-cells to secrete more insulin. When administration of a sulfonylurea or meglitinide becomes ineffective, the amount of insulin in the body can be supplemented by the injection of insulin so that insulin concentrations are high enough to stimulate even the very insulin-resistant tissues. However, dangerously low levels of plasma glucose can result from administration of insulin and/ or insulin secretagogues, and an increased level of insulin resistance due to the even higher plasma insulin levels can occur.

The biguanides are another class of drugs that are widely used to treat type 2 diabetes. The two best known biguanides, phenformin and metformin, cause some correction of hyperglycemia without risk of causing hypoglycemia. The biguanides can be used either with insulin or with an insulin secretagogue without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensititization that is observed with the glitazones. New PPAR agonists are being developed for the treatment of Type 2 diabetes and/or dyslipidemia. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism.

PPAR agonists, and particularly glitazones, have had shortcomings which have so far detracted from their attractiveness. Some of the compounds, and especially troglitazone, have exhibited liver toxicity. Troglitazone was eventually withdrawn from the marketplace because of hepatotoxicity. Another weakness in the currently marketed PPAR agonists is that monotherapy for type 2 diabetes produces only modest efficacy—a reduction in average plasma glucose of ≈20% and a decline from ≈9.0% to ≈8.0% in HemoglobinA1C. The current compounds also do not greatly improve lipid metabolism, and may actually have a negative effect on the lipid profile. These shortcomings have provided an incentive to develop better insulin sensitizers for Type 2 diabetes which function via similar mechanism(s) of action.

Recently, there have been reports of compounds that are PPAR gamma antagonists or partial agonists. WO01/30343 describes a specific compound that is a PPAR partial agonist/antagonist that is useful for the treatment of obesity and Type 2 diabetes. WO02/08188 discloses a class of PPAR agonists and partial agonists that are indole derivatives and that are useful in the treatment of Type 2 diabetes, with reduced side effects relating to body and heart weight gain.

SUMMARY OF THE INVENTION

The class of compounds described herein is a new class of PPAR agonists that do not contain a 1,3-thiazolidinedione moiety. The class of compounds includes many compounds that are PPARγ partial agonists, but also may include PPARγ full agonists and/or PPARγ antagonists. Some compounds may also have PPARα activity in addition to PPARγ activity. Some compounds may be mixed full or partial PPARα/γ agonists. These compounds are useful in the treatment and control of diabetes, hyperglycemia, and insulin resistance.

The compounds may also be useful in the treatment of one or more lipid disorders, including mixed or diabetic dyslipidemia, isolated hypercholesterolemia, which may be manifested by elevations in LDL-C and/or non-HDL-C, hyperapoBliproteinemia, hypertriglyceridemia, an increase in triglyceride-rich-lipoproteins, and low HDL cholesterol concentrations. They may also be useful in the treatment or amelioration of atherosclerosis, obesity, vascular restenosis, inflammatory conditions, psoriasis, polycystic ovary syndrome, and other PPAR mediated diseases, disorders and conditions.

The present invention is directed to compounds of formula I:

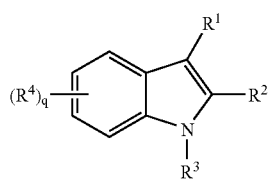

and pharmaceutically acceptable salts and prodrugs thereof.

In the compounds of formula I, $R^1$ is

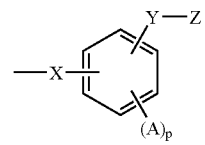

wherein X is selected from the group consisting of a bond, O, $S(O)_n$, CO, $CH_2$, $CH(CH_3)$, $C(CH_3)_2$, and $C_{3-6}$cycloalkylidene;

Y is selected from the group consisting of —CH=CH—, —CH(OH)CH(OH)—, —OCR$^7$R$^8$—, —SCR$^7$R$^8$—, and —CH$_2$CR$^5$R$^6$—;

Z is selected from the group consisting of —CO$_2$H and tetrazole;

A is selected from the group consisting of H, $C_{1-4}$ alkyl, $C_{1-4}$ alkenyl, —O$C_{1-4}$ alkyl, and halogen, wherein alkyl, alkenyl, and Oalkyl are optionally substituted with 1-5 halogens;

$R^5$, $R^6$, $R^7$, and $R^8$ are each independently selected from the group consisting of H, halogen, $C_1$-$C_5$ alkyl, O$C_1$-$C_5$ alkyl, $C_2$-$C_5$ alkenyl, O$C_2$-$C_5$ alkenyl, $C_{3-6}$ cycloalkyl, $(CH_2)_{0-2}$phenyl, —O$(CH_2)_{0-2}$phenyl and CO$_2$H, wherein $C_1$-$C_5$ alkyl, O$C_1$-$C_5$ alkyl, $C_2$-$C_5$ alkenyl, O$C_2$-$C_5$ alkenyl, $C_{3-6}$ cycloalkyl, and phenyl are optionally substituted with 1-5 halogens, and $C_{3-6}$ cycloalkyl and phenyl are further optionally substituted with 1-3 groups independently selected from $C_1$-$C_3$ alkyl and O$C_1$-$C_3$ alkyl, said $C_1$-$C_3$ alkyl and O$C_1$-$C_3$ alkyl being optionally substituted with 1-3 halogens;

Or alternatively $R^7$ and $R^8$ may be connected to form a $C_3$-$C_6$ cycloalkyl group, said $C_3$-$C_6$ cycloalkyl being optionally substituted with 1-3 halogens;

Or alternatively, when Y is OCR$^7$R$^8$, R$^8$ may optionally be a 1-2-carbon bridge connected to the phenyl ring at the position ortho to Y, thereby yielding a 5 or 6-membered heterocyclic ring fused to the phenyl ring;

$R^2$ is $C_1$-$C_4$ alkyl, which is optionally substituted with 1-5 halogens;

$R^3$ is selected from the group consisting of 3-benzisoxazolyl, 3-benzisothiazolyl, and 3-benzpyrazolyl, wherein $R^3$ is optionally substituted with 1-3 groups independently selected from halogen, $C_{1-3}$alkyl, and O$C_{1-3}$alkyl, wherein $C_{1-3}$alkyl and O$C_{1-3}$alkyl are optionally substituted with 1-5 halogens;

Each $R^4$ is independently selected from the group consisting of halogen, $C_1$-$C_3$ alkyl, and O$C_1$-$C_5$ alkyl, wherein $C_1$-$C_3$ alkyl and O$C_1$-$C_5$ alkyl are optionally substituted with 1-5 halogens;

n is an integer from 0-2;

p is an integer from 0-3; and q is an integer from 0-3.

In the above definitions and subsequent definitions, alkyl groups may be either linear or branched, unless otherwise specified.

The present compounds are effective in lowering glucose, lipids, and insulin in diabetic patients and in non-diabetic patients that have impaired glucose tolerance and/or are in a pre-diabetic condition. The compounds are expected to be efficacious in the treatment of non-insulin dependent diabetes mellitus (NIDDM) in human and other mammalian patients, particularly in the treatment of hyperglycemia and in the treatment of conditions associated with NIDDM, including hyperlipidemia, dyslipidemia, obesity, hypercholesterolemia, hypertrigycerigemia, atherosclerosis, vascular restenosis, inflammatory conditions, and other PPAR mediated diseases, disorders and conditions.

DETAILED DESCRIPTION OF THE INVENTION

The invention has numerous embodiments. It provides compounds of formula I, including pharmaceutically acceptable salts of these compounds, prodrugs of these compounds, and pharmaceutical compositions comprising these compounds and a pharmaceutically acceptable carrier.

In preferred subgroups of compounds, q is 1-3. In other preferred subgroups, q is 1.

In preferred subgroups of compounds, p is 1.

In other subgroups, X is selected from the group consisting of a bond, O, $S(O)_n$, $CH_2$, and $C_{3-6}$cycloalkylidene;

Y is selected from the group consisting of $OCR^7R^8$ and $CH_2CR^5R^6$;

Z is selected from $CO_2H$ and tetrazole;

A is selected from the group consisting of H, $CH_3$, $CF_3$, $OCH_3$, $OCF_3$, and halogen;

$R^5$, $R^6$, and $R^7$ are each independently selected from the group consisting of H, halogen, $C_1$-$C_3$ alkyl, and $OC_1$-$C_3$ alkyl, and $R^8$ is selected from the group consisting of halogen, $C_1$-$C_3$ alkyl, and $OC_1$-$C_3$ alkyl, wherein $C_1$-$C_3$ alkyl and $OC_1$-$C_3$ alkyl of $R^5$, $R^6$, $R^7$, and $R^8$ are optionally substituted with 1-3 halogens;

$R^2$ is $C_1$-$C_3$ alkyl;

$R^3$ is selected from the group consisting of 3-benzisoxazolyl, 3-benzisothiazolyl, and 3-benzpyrazolyl, wherein $R^3$ is optionally substituted with 1-3 groups independently selected from halogen, $OCH_3$, $OCF_3$, $CH_3$, and $CF_3$;

Each group $R^4$ is selected from $OCH_3$, $OCF_3$, and $CF_3$;

p is 1; and q is 0-3. Alternatively q may be 1-3; or alternatively, q may be 1.

In subsets of the above subgroups, $R^5$, $R^6$, and $R^7$ are each independently selected from the group consisting of H, halogen, $C_1$-$C_3$ alkyl, and $OC_1$-$C_3$ alkyl, and $R^8$ is selected from the group consisting of halogen, $C_1$-$C_3$ alkyl, and $OC_1$-$C_3$ alkyl.

In other groups of compounds, X may be O, $S(O)_n$, or $CH_2$;

Y may be $OCR^7R^8$ or $CH_2CR^5R^6$;

Z is $CO_2H$;

A is selected from the group consisting of H, $CH_3$, $CF_3$, $OCH_3$, $OCF_3$, and halogen;

$R^5$ is H;

$R^6$ is selected from H and $OC_1$-$C_3$ alkyl, which is optionally substituted with 1-3 halogens;

$R^7$ is selected from the group consisting of H and $C_1$-$C_3$ alkyl;

$R^8$ is $C_1$-$C_3$ alkyl;

$R^2$ is selected from $C_1$-$C_3$ alkyl and $CF_3$; and $R^3$ is selected from 3-benzisoxazolyl, 3-benzisothiazolyl, and 3-benzpyrazolyl, wherein $R^3$ is optionally substituted with 1 groups independently selected from halogen, $OCH_3$, $OCF_3$, $CH_3$, and $CF_3$.

In many sub-groups of compounds, $R^2$ is $C_{1-3}$ alkyl. $R^2$ is preferably $CH_3$.

In many preferred sub-groups of compounds, X is O.

In other preferred sub-groups of compounds, X is $CH_2$.

In other preferred sub-groups of compounds, X is S.

In other preferred sub-groups of compounds, X is S(O).

In other preferred sub-groups of compounds, X is $S(O)_2$.

In many sub-groups of preferred compounds, Y is $OCR^7R^8$; $R^7$ is selected from H and $C_1$-$C_3$ alkyl; and $R^8$ is $C_1$-$C_3$ alkyl.

In other preferred sub-groups, Y is $CH_2CHR^5$, where $R^5$ is $OC_1$-$C_3$ alkyl, which is optionally substituted with 1-3 halogens.

In many preferred compounds, Z is $CO_2H$.

In many sub-groups of compounds, A is selected from the group consisting of H, $CH_3$, $CF_3$, $OCH_3$, $OCF_3$, and halogen.

In some preferred embodiments, $R^3$ is 3-benzisoxazolyl, which is optionally substituted with 1-3 substituents independently selected from halogen, $OCH_3$, $OCF_3$, $CH_3$, and $CF_3$.

In some preferred embodiments, $R^3$ is 3-benzisoxazolyl, which is optionally substituted with 1 substituent selected from halogen, $OCH_3$, $OCF_3$, and $CF_3$.

In one group of preferred compounds, $R^4$ is selected from $OCH_3$, $OCF_3$, and $CF_3$;

X is selected from O and $CH_2$;

Y is $OC^*R^7R^8$, wherein $R^7$ is H and $R^8$ is $C_1$-$C_3$ alkyl; and

Z is $CO_2H$;

A is selected from the group consisting of H, $CH_3$, $CF_3$, $OCH_3$, $OCF_3$, and halogen;

X and YZ are meta to each other on the phenyl ring of $R^1$;

$R^2$ is $CH_3$;

$R^3$ is 3-benzisoxazolyl, which is optionally substituted with 1 substituent selected from halogen, $OCH_3$, $OCF_3$, and $CF_3$; and q is 1.

In the above compounds, C* represents an asymmetric carbon. Compounds having both the R and S stereochemical configuration have activity as PPAR gamma agonists. The activities are different for each stereochemical configuration, with variations in the relative amounts of PPAR alpha agonism and PPAR gamma agonism.

Structures of specific compounds are disclosed in Table 1. The names are provided for the compounds in separate Table 1A. Each compound is given the same number in the two tables. Each compound is a specific embodiment of the current invention. The syntheses of some of these compounds are also provided in the Examples.

The compounds of this invention can be used in pharmaceutical compositions comprising the compound or a pharmaceutically acceptable salt thereof and a pharmaceutically acceptable carrier. The compounds of this invention can also be used in pharmaceutical compositions in which a compound of Formula I or a pharmaceutically acceptable salt thereof is the only active ingredient.

The compounds of the invention and pharmaceutically acceptable salts thereof can be used in the manufacture of medicaments for the treatment of type 2 diabetes mellitus in a human or other mammalian patient.

Compound 20 in Tables 1 and 1A of this application was also disclosed in a provisional application which was filed after the filing dates of the two US Provisional Applications from which priority is claimed in this application, to illustrate the use of this compound in the invention disclosed in the later application. It is to be understood that the invention herein includes the generic claims as written, and furthermore includes each of the generic claims with a disclaimer of the specific compound listed above.

The compounds as defined above may be used in the following methods to treat diseases, as well as other diseases not listed below:

(1) a method for treating non-insulin dependent diabetes mellitus (type 2 diabetes) in a human or other mammalian patient in need of such treatment which comprises administering to the patient a therapeutically effective amount of a compound of Formula I;

(2) a method for treating or controlling hyperglycemia in a human or other mammalian patient in need of such treatment which comprises administering to the patient a therapeutically effective amount of a compound of Formula I;

(3) a method for treating or controlling the metabolic syndrome in a human or other mammalian patient in need of such treatment which comprises administering to the patient a therapeutically effective amount of a compound of Formula I;

(4) a method for treating or controlling obesity in a human or other mammalian patient in need of such treatment which comprises administering to the patient a therapeutically effective amount of a compound of Formula I;

(5) a method for treating or controlling hypercholesterolemia in a human or other mammalian patient in need of such treatment which comprises administering to the patient a therapeutically effective amount of a compound of Formula I;

(6) a method for treating or controlling hypertriglyceridemia in a human or other mammalian patient in need of such treatment which comprises administering to the patient a therapeutically effective amount of a compound of Formula I;

(7) a method for treating or controlling one or more lipid disorders, including mixed or diabetic dyslipidemia, low HDL cholesterol, high LDL cholesterol, hyperlipidemia, hypercholesterolemia, and hypertriglyceridemia in a human or other mammalian patient in need of such treatment which comprises administering to the patient a therapeutically effective amount of a compound of Formula I;

(8) a method for reducing the risks of adverse sequelae associated with metabolic syndrome in a human or other mammalian patient in need of such treatment which comprises administering to the patient a therapeutically effective amount of a compound of Formula I; and (9) a method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

The compounds are especially useful in the treatment of the following diseases, by administering a therapeutically effective amount to a patient in need of treatment:

(1) type 2 diabetes, and especially hyperglycemia;
(2) metabolic syndrome;
(3) obesity; and
(4) hypercholesterolemia.

Definitions

"Ac" is acetyl, which is $CH_3C(O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each having from 3 to 10 carbon atoms, unless otherwise stated. The term also includes a monocyclic ring fused to an aryl group. Examples of cycloalkyl include cyclopropyl, cyclopentyl, cyclohexyl, cycloheptyl, and the like.

A cycloalkylidene group is a divalent cycloalkane radical in which both attachments are at the same carbon. For example, the cyclopropyl group of 1,1-dimethylcyclopropane is a cyclopropylidene group.

"Aryl" (and "arylene") when used to describe a substituent or group in a structure means a monocyclic, bicyclic or tricyclic compound in which all the rings are aromatic and which contains only carbon ring atoms. The term "aryl" can also refer to an aryl group that is fused to a cycloalkyl or heterocycle. "Heterocyclyl," "heterocycle," and "heterocyclic" means a fully or partially saturated monocyclic, bicyclic or tricyclic ring system containing at least one heteroatom selected from N, S and O, each of said rings having from 3 to 10 atoms. Examples of aryl substitiuents include phenyl and naphthyl. Aryl rings fused to cycloalkyls are found in indanyl, indenyl, and tetrahydronaphthyl. Examples of aryl fused to heterocyclic groups are found in 2,3-dihydrobenzofuranyl, benzopyranyl, 1,4-benzodioxanyl, and the like. Examples of heterocycles include tetrahydrofuran, piperazine, and morpholine. Preferred aryl groups are phenyl or naphthyl. Phenyl is generally the most preferred.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of the Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites of other compounds, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention. A non-limiting example of a prodrug of the carboxylic acids of this invention would be an ester of the carboxylic acid group, for example a $C_1$ to $C_6$ ester, which may be linear or branched, which metabolizes to a carboxylic acid of this invention. An ester which has functionality that makes it more easily hydrolyzed after administration to a patient may also be a prodrug.

Prodrugs of the class of compounds of this invention may be described as compounds having the Formula I, wherein Z is a group that is easily metabolized under physiological conditions during or after administration to a mammalian or human patient to yield a compound where Z is a carboxylic acid group, or a salt thereof (in solution).

Examples of prodrugs of Formula I include compounds in which Z is —$CO_2R^a$, where the $OR^a$ group can be —$OR^b$, —$OCH_2OR^b$, —$OCH(CH_3)OR^b$, —$OCH_2OC(O)R^b$, —$OCH(CH_3)OC(O)R^b$, —$OCH_2OC(O)OR^b$, and —$OCH(CH_3)OC(O)OR^b$, where $OR^b$ is selected from $C_{1-6}$ alkyl optionally substituted with one or two groups selected from —$CO_2H$, —$CONH_2$, —$NH_2$, —OH, —OAc, NHAc, and phenyl.

Utilities

Compounds of the present invention are potent ligands having agonist, partial agonist or antagonist activity on one or more of the various peroxisome proliferator activated receptor subtypes, particularly PPARγ. The compounds may also be ligands or agonists, partial agonists or antagonists of the PPARα subtype as well as the PPARγ subtype, resulting in mixed PPARα/γ agonism or in agonism of mainly the PPARα subtype. Some compounds (generally less preferred) may also be PPARδ ligands and have PPARδ activity in addition to their other PPAR activity. The compounds of this invention are useful in treating or controlling diseases, disorders or conditions which are mediated by one or more ligands of the individual PPAR subtypes (eg. γ or α) or a combination of PPAR subtypes (e.g. α/γ). One aspect of the present invention provides a method for the treatment and control of diseases that can be mediated by administration of a PPAR agonist or partial agonist, such as type 2 diabetes. One aspect of the present invention provides a method for the treatment and control of such diseases, disorders, or conditions in a mammal which comprises administering to such mammal a therapeutically effective amount of a compound of Formula I. Compounds of the present invention may be useful in treating or controlling many PPAR mediated diseases and conditions, including, but not limited to, (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) psoriasis, (23) metabolic syndrome, (24) ovarian hyperandrogenism (polycystic ovarian syndrome), and other disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers, angiogenesis, and Alzheimer's disease.

The compounds may also have utility in treating osteoporosis. The compounds of this invention may treat osteoporosis or reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors, niacin, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 1 milligram to about 350 milligrams. For a particularly potent compound, the dosage for an adult human may be as low as 0.1 mg. This dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, and 250 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure;

(b) biguanides such as metformin and phenformin;

(c) protein tyrosine phosphatase-1B (PTP-1B) inhibitors, (d) dipeptidyl peptidase IV (DP-IV) inhibitors;

(e) insulin or insulin mimetics;

(f) sulfonylureas such as tolbutamide and glipizide, or related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, and (viii) phenolic anti-oxidants, such as probucol;

(i) PPARα/γ dual agonists, such as KRP-297;

(j) PPARδ agonists such as those disclosed in WO97/28149;

(k) antiobesity compounds such as fenfluramnine, dexfenfluramine, phentiramine, subitramine, orlistat, neuropeptide Y5 inhibitors, Mc4r agonists, cannabinoid receptor 1 (CB-1) antagonists/inverse agonists, and $\beta_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, and (q) GLP-1 analogs, such as exendins.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PIP-1B inhibitors, DP-IV inhibitors, and anti-obesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in E. coli. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). E. coli containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C. For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 μL. Unbound ligand was removed by incubation with 100 μL dextranigelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ±test compound as described in Berger et al (Novel peroxisome proliferator-activated receptorγ (PPARγ) and PPARδ ligands produce distinct biological effects.1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34 Ci/mmole), ±test compound. (L-797733 is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with a full PPAR agonist, such as rosiglitazone. Generally, if the maximal stimulation of transactivation is less than 50% of the effect observed with a full agonist, then the compound is designated as a partial agonist. If the maximal stimulation of transactivation is greater than 50% of the effect observed with a full agonist, then the compound is designated as a full agonist. The compounds of this invention have EC50 values in the range of 1 nM to 3000 nM.

C) In Vivo Studies

Male db/db mice (10-11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3-5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

EXAMPLES

The following Examples are provided to illustrate the invention and are not to be construed as limiting the invention in any manner. The scope of the invention is defined by the appended claims.

Tables 1 and 1A list compounds that correspond to formula I that have been made, including characterization data for each compound. NMR data were also obtained for each compound. The syntheses of representative compounds are presented below. The remaining compounds can be made by one of skill in the art using analogous methodology and readily available starting materials and reagents.

Synthesis of Dicholorobenzisoxazole Intermediate 12

See the Scheme that appears after this synthesis for an overview of this synthesis and the synthesis used in Example 1.

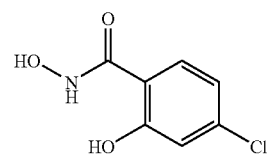

Hydroxamic acid 10: Hydroxyl amine hydrochloride (13.0 gr, 200 mmol) in water (150 mL) was added dropwise to aqueous sodium hydroxide (14.07 gr, 351.8 mmol, in 53 mL water). To this solution was added ester 9 (18.75 gr, 100.5 mmol) in dioxane (50 mL). The reaction was stirred for 18 h then concentrated in vacuo. The aqueous mixture was acidified to pH 1 and the ppt. was filtered and dried. The solid was recrystallized from hot methanol to afford an off-white solid.

$^1$H-NMR (d$_6$-DMSO, 500 MHz) δ 9.40 (br s, 1H), 7.67 (d, 1H), 6.97 (d, 1H), 6.93 (dd, 1H).

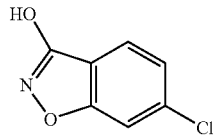

3-hydroxy benzisoxazole 11: Carbonyldiimidazole was carefully added in portions to a hot solution of hydroxamic acid 10 (12.81 gr, 68.3 mmol) in tetrahydrofuran (200 mL). After refluxing for 3 h the reaction was cooled to room temperature and diluted with ethylacetate then extracted with 1N hydrochloric acid (1×), water (2×) and brine (1×). The organic layer was washed with water (2×), brine (1×) then dried with magnesium sulfate, filtered and evaporated to afford 10 as a solid that was recrystallized from hot methanol to afford a white solid; $^1$H-NMR (d$_6$-DMSO, 500 MHz) δ 7.79-7.72 (m, 2H), 7.35 (d, 1H).

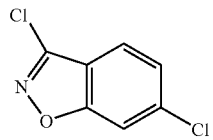

3-Chlorobenzisoxazole 12: 2-Hydroxy benzisoxazole 11 (1.03 gr, 6.25 mmol), triethylamine (632 mg, 6.25 mmol) and phosphorousoxychloride (1.92 gr, 12.5 mmol) were heated in a sealed tube at 150° C. for 18 h. After this time the reaction was cooled to room temperature and diluted with ether and carefully quenched with excess ice/water. The resulting mixture was stirred for 15 min then the organic layer was washed with water (2×), brine (1×), dried with magnesium sulfate, filtered and evaporated to afford 12 as a white solid after column chromatography (hexanes/ethyl acetate, 97:3); $^1$H-NMR (CDCl$_3$, 500 MHz) δ 7.65-7.63 9 m, 2H), 7.42 (dd, 1H).

SCHEME

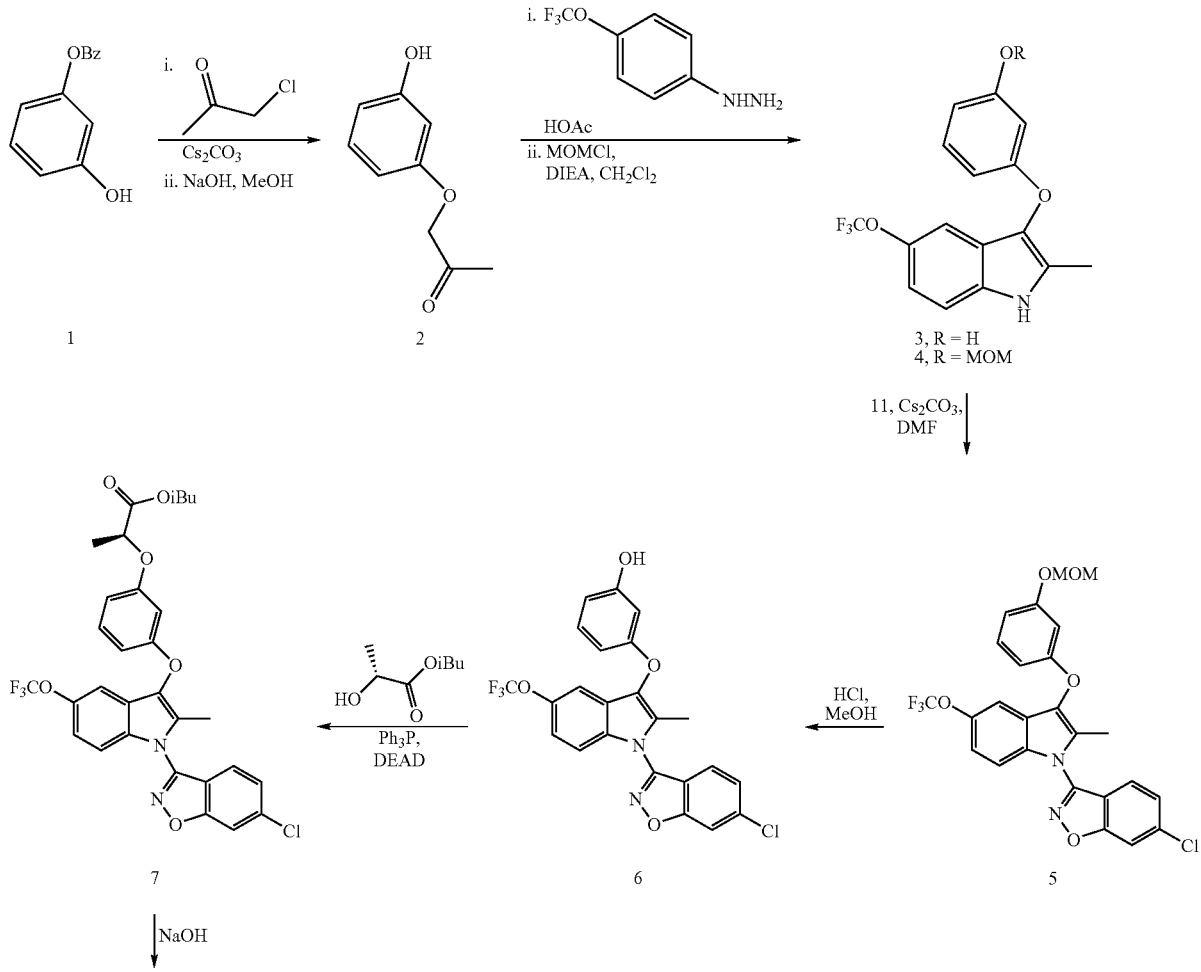

-continued

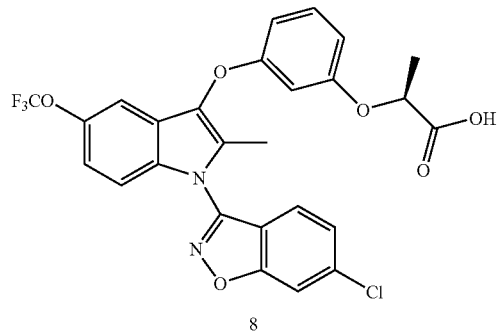

8

Synthesis of 12

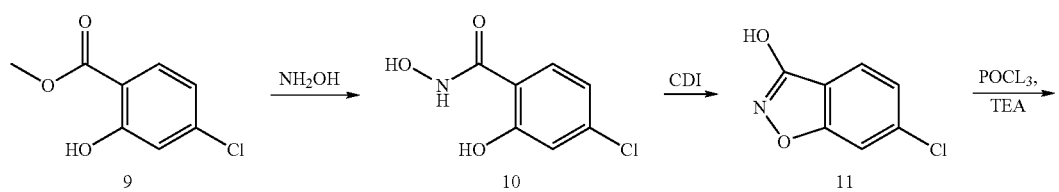

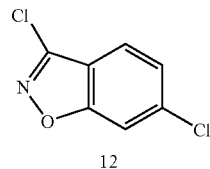

12

Example 1

Compounds Numbered 8 and 9 in this Example

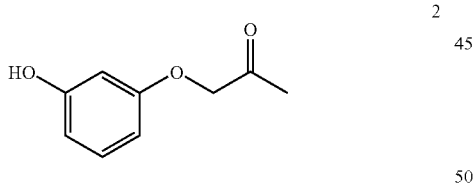

2

Ketone 2: A suspension of chloroacetone (4.44 gr, 48 mmol, the chloroacetone was filtered through basic alumina prior to use), phenol 1 (6.85 gr, 32 mmole) and cesium carbonate (16.9, 48 mmol) was stirred in DMF at room temperature under nitrogen atmosphere for 2 h. After this time the reaction was diluted with ether then washed with water (4×) and Brine (1×). The ether layer was dried with magnesium sulfate, filtered and evaporated to afford a white solid that was taken up in MeOH then treated with 1N NaOH. After 1 hr, excess MeOH was removed under reduced pressure and the residue was dissolved in ether then acidified with 1N HCl. The ether layer was washed with $H_2O$ (2×) and brine (1×), dried with magnesium sulfate, filtered and evaporated to afford an oil after column chromatography (hexanes/ethyl acetate, 4:1); $^1$H-NMR (CDCl$_3$, 500 MHz) δ 7.18 (t, 1H), 6.51-6.49 (m, 2H), 6.43 (s, 1H), 5.05 (br s, 1H), 5.59 (s, 2H), 2.29 (s, 3H).

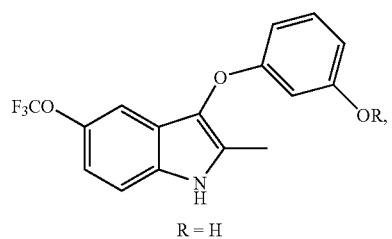

3

R = H

Indole 3: Ketone 2 (3.65 gr, 17 mmol) and 4-trifluoromethoxy phenylhydrazine hydrochloride (4.66 gr, 20.4 mmol) were stirred at reflux in acetic acid (0.25M) for 1 h under nitrogen atmosphere. The reaction was cooled to room temperature the acetic acid was removed under reduced pressure and the residue was diluted with ether and washed with water (1×) and brine (1×). The ether layer was dried with magnesium sulfate, filter and evaporated to afford 3 as a yellow oil after column chromatography (hexanes/ethyl acetate, 4:1); $^1$H-NMR (CDCl$_3$, 500 MHz) δ 7.79 (br s, 1H), 7.25 (d, 1H), 7.17 (s, 1H), 7.14 (t, 1H), 7.03 (dd, 1H), 6.58 (dd, 1H), 6.50 (dd, 1H), 6.44 (t, 1H), 4.95 (br s, 1H), 2.33 (s, 1H).

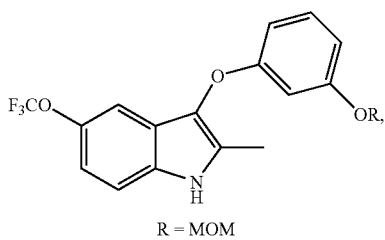

4

R = MOM

MOM protected indole 4: A solution of indole 3 (1.72 gr, 5.1 mmol), MOMCl (6.1 mmol) and diisopropyl ethylamine (7.9 mmol) was stirred under nitrogen atmosphere for 3 hr. after this time the reaction was diluted with ether then the ether layer was washed with water and brine. The organic layer was dried with magnesium sulfate, filtered and evaporated to afford a light yellow oil after column chromatography (hexanes/ethyl acetate, 4:1); $^1$H-NMR (CDCl$_3$, 500 MHz) δ 7.76 (br s, 1H), 7.26 (d, 1H), 7.17 (m, 2H), 7.03 (dd, 1H), 6.74 (dd, 1H), 6.69 (t, 1H), 6.61 (dd, 1H), 5.16 (s, 2H), 3.48 (s, 3H), 2.36 (s, 3H).

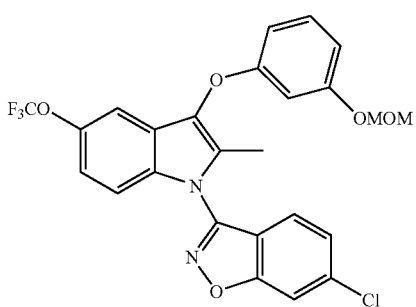

5

Benzisoxazole 5: A solution of indole 4 (565 mg, 1.52 mmol), benzisoxazole 12 (310 mg, 1.67 mmol)and cesium carbonate (1.34 gr, 3.8 mmol) was dissolved in DMF (7.6 mL) and degassed. The resulting mixture was heated at 150° C. for 20 h. After this time the reaction was cooled to room temperature, diluted with ether, washed with water (3×) and brine (1×). The ether layer was dried with magnesium sulfate, filtered and evaporated to afford a light yellow oil after column chromatography (hexanes/ethyl acetate, 95:5); $^1$H-NMR (CDCl$_3$, 500 MHz) δ 7.79 (s, 1H), 7.57 (d, 1H), 7.42 (d, 1H), 7.31 (d, 1H), 7.25 (s, 1H), 7.23 (t, 1H), 7.19 (d, 1H), 6.80-6.71 9 m, 2H), 6.69 9 dd, 1H), 5.18 (s, 2H), 3.48 (s, 3H), 2.38 9 s, 3H).

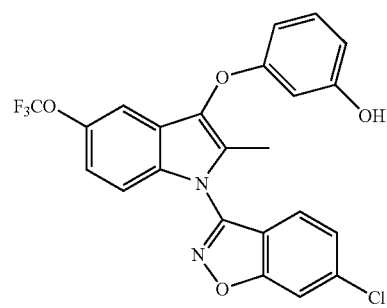

6

Phenol 6: Boron tribromide (2.04 ml, 1.0 M in methylene chloride) was added dropwise to a solution of N-benzisoxazole 5 (525 mg, 1.02 mmol) in methylene chloride (3 mL) stirring at reduced temperature under nitrogen atmosphere. The reaction was warmed to room temperature with stirring over 4 h. The reaction was diluted with ether and quenched by the addition of ice/water (3 gr/3 mL). The resulting mixture was stirred for 15 min then extracted with water (1×) and brine (1×). The ether layer was dried with magnesium sulfate, filtered and evaporated to afford 5 as a light yellow oil after column chromatography (hexanes/ethyl acetate, 85:15); $^1$H-NMR (CDCl$_3$, 500 MHz) δ 7.79 9 d, 1H), 7.55 (d, 1H), 7.43 9 dd, 1H), 7.31 (t, 1H), 7.26 s, 1H), 7.18 (d, 1H), 7.09 (dd, 1H), 6.65 9 dd, 1H), 6.57-6.54 9 m, 2H), 5.04 (br s, 1H), 2.40 (s, 3H).

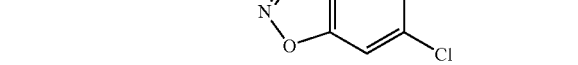

7

S-lactate 7: Diethyl azidodicarboxylate (217 mg, 1.25 mmol) was added dropwise to a stirring solution of the phenol 6 (458 mg, 0.899 mmol), isobutyl (R)-lactate (183 mg, 1.25 mmol) and triphenylphosphine (330 mg, 1.25 mmol) in methylene chloride at room temperature under nitrogen atmosphere. After 1 h, the reaction was diluted with ether and washed with water (2×) and brine (1×). The ether layer was dried with magnesium sulfate, filter and evaporated to afford 6 as a light yellow oil after column chromatography (hexanes/ ethyl acetate, 9:1); $^1$H-NMR (CDCl$_3$, 500 MHz) δ 7.79 (d, 1H), 7.57 (d, 1H), 7.44 (dd, 1H), 7.31 (d, 1H), 7.23 (s, 2H), 7.20 (d, 1H), 7.09 (dd, 1H), 6.67 (dd, 1H), 6.62 (t, 1H), 6.59 (dd, 1H), 4.78 (q, 1H), 3.98 (dd, 1H), 3.89 (dd, 1H), 2.38 (s, 3H), 1.92 (sept., 1H), 1.63 (d, 3H), 0.88 (d, 6H).

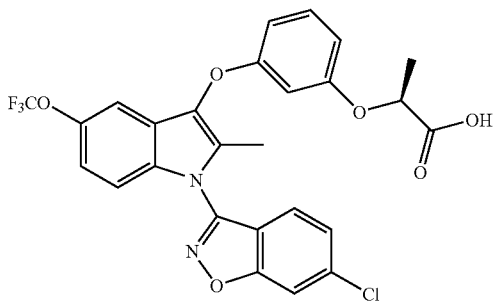

Acid 8: The (S)-lactate 7 (495 mg, 0.777 mmol) and aqueous sodium hydroxide (0.935 mL, 1.0M) were stirred in tetrahydrofuran and methanol (3:1) at room temperature for 18 h. After this time the reaction was diluted with ether and acidified to about pH 3-4 with 1N aqueous hydrochloric acid. The organic layer was washed with water (2×), brine (1×) then dried with magnesium sulfate, filtered and evaporated to afford 8 as a colorless oil that solidified upon standing after column chromatography (hexanes/ethyl acetate/acetic acid, 7:3:0.1). $^1$H-NMR (CDCl$_3$, 500 MHz) δ 7.78 (d, 1H), 7.56 (d, 1H), 7.43 (dd, 1H), 7.32-7.22 (m, 3H), 7.09 (d, 1H), 6.70 (d, 1H), 6.63-6.60 (m, 2H), 4.80 (q, 1H), 2.38 (s, 3H), 1.67 (d, 3H).

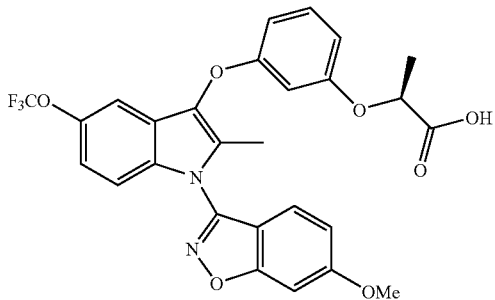

6-Methoxybenzisoxazole 9: Acid 8 (865 mg, 1.43 mmol) was dissolved in methanol and 0.95 equivalents of aq. NaHCO$_3$ (1.41 ml, 1M) was added. The resulting solution was stirred for 15 minutes and then the methanol was removed by evaporation to give the sodium salt. The salt was taken up in ethanol and concentrated several times to remove all traces of water. The sodium salt was then dissolved in DMW (6 ml) and sodium methoxide (4.3 ml, 0.5 M in methanol) was added. The reaction was heated at 100° C. overnight. After this time, the reaction was diluted with ethyl acetate and washed with 1N HCl (2×), water (1×), brine (1×), dried with sodium sulfate, filtered and evaporated to give 9 as an oil after column chromatography (ethyl acetate/hexanes/1% acetic acid, gradient from 5% to 100% ethyl acetate over 10 column volumes). $^1$H-NMR (CDCl$_3$, 500 MHz) δ 7.46 (d, 1H), 7.40 (d, 1H), 7.34 (d, 1H), 7.29 (d, 1H), 7.16 (d, 1H), 7.10 (dd, 1H), 7.06 (dd, 1H), 6.56 (dd, 1H), 6.46 (d, 1H), 4.63 (q, 1H), 4.00 (s, 3H), 2.39 (s, 3H), 1.59 (d, 3H).

Examples 2-11

The following compounds were prepared in a similar fashion to the compounds above using commercially available starting materials and reagents. These can be made by a practitioner in the field of organic chemistry using the methods and strategies disclosed herein.

Example 2

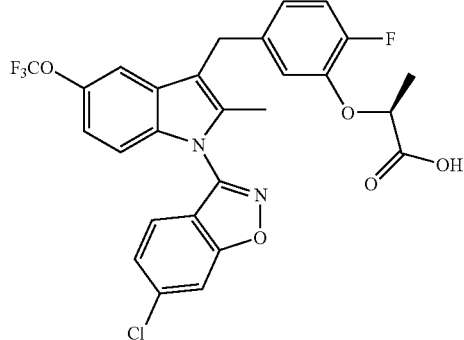

(2S)-2-(5-{[1-(6-chloro-1,2-benzisoxazol-3-yl)-2-methyl-5-(trifluoromethoxy)- 1H-indol-3-yl]methyl}-2-fluorophenoxy)propanoic acid $^1$H NMR (500 MHz, CDCl$_3$): δ 7.78 (d, Ar, 1H), 7.52 (d, Ar, 1H), 7.41 (dd, Ar, 1H), 7.28 (br s, Ar, 1H), 7.23 (d, Ar, 1H), 7.05 (m, Ar, 2H), 6.90 (m, Ar, 1H), 6.83 (dd, Ar, 1H), 4.73 (q, OC$\underline{H}$(CH$_3$)COOH, 1H), 4.10 (q, C$\underline{H_2}$Ar, 2H), 2.41 (s, 2-Me, 3$\underline{H}$), 1.65 (d, OCH(C$\underline{H_3}$)COOH, $\overline{3H}$).

RP LC/MS: $t_R$=4.48 min, m/e 563 (M+1).

Example 3

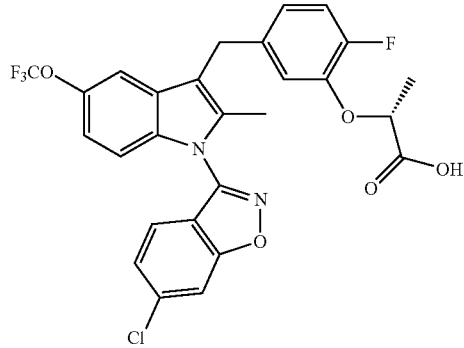

(2R)-2-(5-{[1-(6-chloro-1,2-benzisoxazol-3-yl)-2-methyl-5-(trifluoromethoxy)-1H-indol-3-yl]methyl}-2-fluorophenoxy)propanoic acid $^1$H NMR (500 MHz, CDCl$_3$): δ 7.78 (d, Ar, 1H), 7.52 (d, Ar, 1H), 7.41 (dd, Ar, 1H), 7.28 (br s, Ar, 1H), 7.23 (d, Ar, 1H), 7.05 (m, Ar, 2H), 6.90 (m, Ar, 1H), 6.83 (dd, Ar, 1H), 4.73 (q, OC$\underline{H}$(CH$_3$)COOH, 1H), 4.10 (q, C$\underline{H_2}$Ar, 2H), 2.41 (s, 2-Me, 3$\underline{H}$), 1.65 (d, OCH(C$\underline{H_3}$)COOH, $\overline{3H}$).

RP LC/MS: $t_R$=4.48 min, n/e 563 (M+1).

Example 4

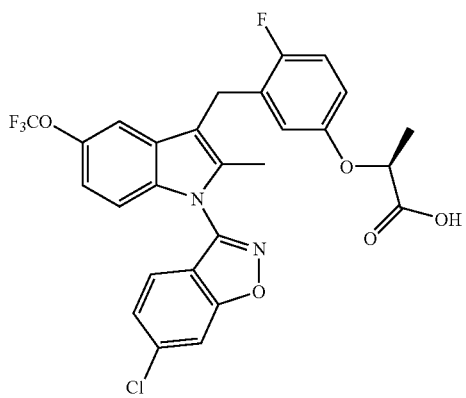

(2S)-2-(3-{[1-(6-chloro-1,2-benzisoxazol-3-yl)-2-methyl-5-(trifluoromethoxy)-1H-indol-3-yl]methyl}-4-fluorophenoxy)propanoic acid $^1$H NMR (500 MHz, CDCl$_3$): δ 7.78 (d, Ar, 1H), 7.53 (d, Ar, 1H), 7.41 (dd, Ar, 1H), 7.37 (br s, Ar, 1H), 7.22 (d, Ar, 1H), 7.05 (br d, Ar, 1H), 7.02 (t, Ar, 1H), 6.72 (m, Ar, 1H), 6.64 (m, Ar, 1H), 4.60 (q, OCH(CH$_3$)COOH, 1H), 4.10 (s, CH$_2$Ar, 2H), 2.43 (s, 2-Me, 3H), 1.58 (d, OCH(CH$_3$)COOH, 3H).

RP LC/MS: t$_R$=4.47 min, m/e 563 (M+1).

Example 5

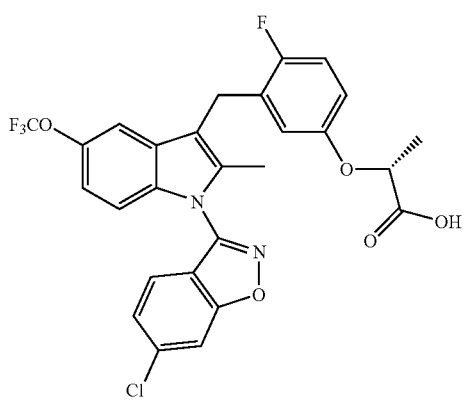

(2R)-2-(3-{[1-(6-chloro-1,2-benzisoxazol-3-yl)-2-methyl-5-(trifluoromethoxy)-1H-indol-3-yl]methyl}-4-fluorophenoxy)propanoic acid $^1$H NMR (500 MHz, CDCl$_3$): δ 7.78 (d, Ar, 1H), 7.53 (d, Ar, 1H), 7.41 (dd, Ar, 1H), 7.37 (br s, Ar, 1H), 7.22 (d, Ar, 1H), 7.05 (br d, Ar, 1H), 7.02 (t, Ar, 1H), 6.72 (m, Ar, 1H), 6.64 (m, Ar, 1H), 4.60 (q, OCH(CH$_3$)COOH, 1H), 4.10 (s, CH$_2$Ar, 2H), 2.43 (s, 2-Me, 3H), 1.58 (d, OCH(CH$_3$)COOH, 3H).

RP LC/MS: t$_R$=4.47 min, m/e 563 (M+1).

Example 6

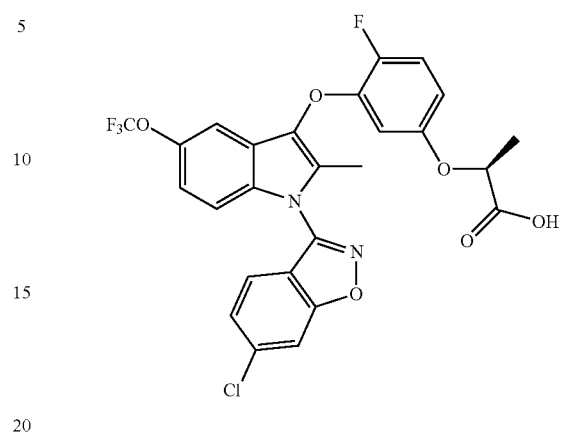

(2S)-2-(3-{[1-(6-chloro-1,2-benzisoxazol-3-yl)-2-methyl-5-(trifluoromethoxy)-1H-indol-3-yl]oxy-}4-fluorophenoxy)propanoic acid $^1$H NMR (500 MHz, CDCl$_3$): δ 7.79 (d, Ar, 1H), 7.57 (d, Ar, 1H), 7.44 (dd, Ar, 1H), 7.30 (d, Ar, 1H), 7.29 (br s, Ar, 1H), 7.15 (dd, Ar, 1H), 7.10 (dd, Ar, 1H), 6.50 (dt, Ar, 1H), 6.47 (dd, Ar, 1H), 4.62 (q, OCH(CH$_3$)COOH, 1H), 2.39 (s, 2-Me, 3H), 1.57 (d, OCH(CH$_3$)COOH, 3H).

RP LC/MS: t$_R$=4.42 min, m/e 565 (M+1).

Example 7

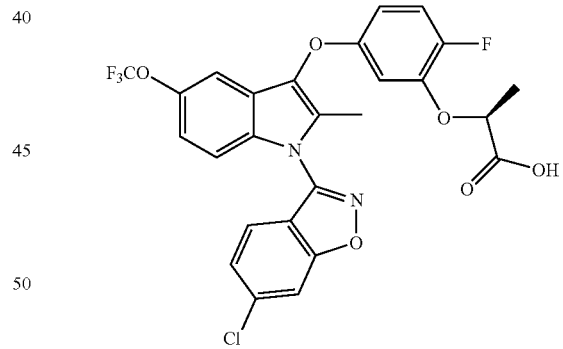

(2S)-2-(5-{[1-(6-chloro-1,2-benzisoxazol-3-yl)-2-methyl-5-(trifluoromethoxy)-1H-indol-3-yl]oxy}-2-fluorophenoxy)provanoic acid $^1$H NMR (500 MHz, CDCl$_3$): δ 7.80 (d, Ar, 1H), 7.57 (d, Ar, 1H), 7.44 (dd, Ar, 1H), 7.30 (d, Ar, 1H), 7.23 (br s, Ar, 1H), 7.10 (dd, Ar, 1H), 7.06 (dd, Ar, 1H), 6.70 (dd, Ar, 1H), 6.64 (dt, Ar, 1H), 4.78 (q, OCH(CH$_3$)COOH, 1H), 2.36 (s, 2-Me, 3H), 1.69 (d, OCH(CH$_3$)COOH, 3H).

RP LC/MS: t$_R$=4.38 min, m/e 565 (M+1).

Example 8

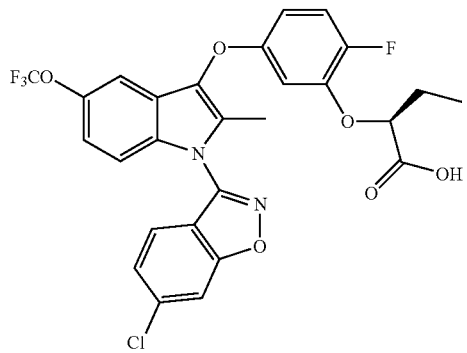

(2S)-2-(5-{[1-(6-chloro-1,2-benzisoxazol-3-yl)-2-methyl-5-(trifluoromethoxy)-1H-indol-3-yl]oxy}-2-fluorophenoxy)butanoic acid $^1$H NMR (500 MHz, CDCl$_3$): δ 7.77 (d, Ar, 1H), 7.54 (d, Ar, 1H), 7.41 (dd, Ar, 1H), 7.30 (d, Ar, 1H), 7.21 (br s, Ar, 1H), 7.08 (dd, Ar, 1H), 7.02 (dd, Ar, 1H), 6.69 (dd, Ar, 1H), 6.59 (dt, Ar, 1H), 4.60 (t, OC<u>H</u>(CH$_2$CH$_3$)COOH, 1H), 2.33 (s, 2-Me, 3H), 2.04 (m, OCH(C<u>H$_2$</u>CH$_3$)COOH, 2H), 1.10 (t, OCH(CH$_2$C<u>H$_3$</u>)COOH, 3H).

RP LC/MS: $t_R$=4.51 min, n/e 579 (M+1).

Example 9

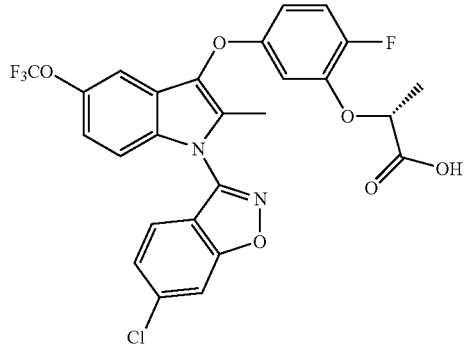

(2R)-2-(5-{[1-(6-chloro-1,2-benzisoxazol-3-yl)-2-methyl-5-(trifluoromethoxy)-1H-indol-3-yl]oxy}-2-fluorophenoxy)propanoic acid $^1$H NMR (500 MHz, CDCl$_3$): δ 7.80 (d, Ar, 1H), 7.57 (d, Ar, 1H), 7.44 (dd, Ar, 1H), 7.30 (d, Ar, 1H), 7.23 (br s, Ar, 1H), 7.10 (dd, Ar, 1H), 7.06 (dd, Ar, 1H), 6.70 (dd, Ar, 1H), 6.64 (dt, Ar, 1H), 4.78 (q, OCH(CH$_3$)COOH, 1H), 2.36 (s, 2-Me, 3H), 1.69 (d, OCH(C<u>H$_3$</u>)COOH, 3H).

RP LC/MS: $t_R$=4.38 min, m/e 565 (M+1).

Example 10

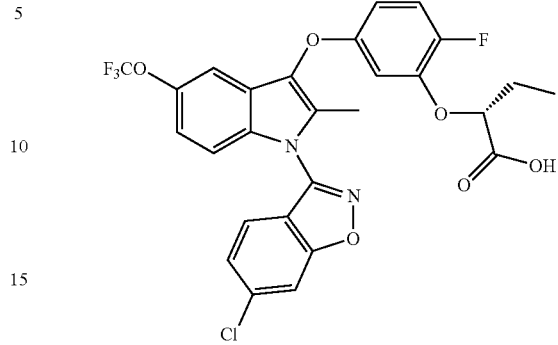

(2R)-2-(5-{[1-(6-chloro-1,2-benzisoxazol-3-yl)-2-methyl-5-(trifluoromethoxy)-1H-indol-3-yl]oxy}-2-fluorophenoxy)butanoic acid $^1$H NMR (500 MHz, CDCl$_3$): δ 7.77 (d, Ar, 1H), 7.54 (d, Ar, 1H), 7.41 (dd, Ar, 1H), 7.30 (d, Ar, 1H), 7.21 (br s, Ar, 1H), 7.08 (dd, Ar, 1H), 7.02 (dd, Ar, 1H), 6.69 (dd, Ar, 1H), 6.59 (dt, Ar, 1H), 4.60 (t, OCH(CH$_2$CH$_3$)COOH, 1H), 2.33 (s, 2-Me, 3H), 2.04 (m, OC<u>H</u>(CH$_2$CH$_3$)COOH, 2H), 1.10 (t, OCH(CH$_2$CH$_3$)COOH, 3H).

RP LC/MS: $t_R$=4.51 min, m/e 579 (M+1).

Example 11

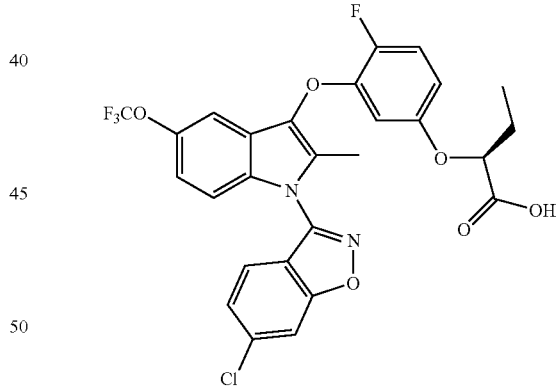

(2S)-2-(3-{[1-(6-chloro-1,2-benzisoxazol-3-yl)-2-methyl-5-(trifluoromethoxy)-1H-indol-3-yl]oxy}-4-fluorophenoxy)butanoic acid $^1$H NMR (500 MHz, CDCl$_3$): δ 7.78 (d, Ar, 1H), 7.56 (d, Ar, 1H), 7.43 (dd, Ar, 1H), 7.29 (d, Ar, 1H), 7.28 (br s, Ar, 1H), 7.13 (t, Ar, 1H), 7.09 (dd, Ar, 1H), 6.51 (dt, Ar, 1H), 6.47 (dd, Ar, 1H), 4.43 (t, OCH(CH$_2$CH$_3$)COOH, 1H), 2.37 (s, 2-Me, 3H), 1.93 (m, OC<u>H</u>(CH$_2$CH$_3$)COOH, 2H), 1.01 (t, OCH(CH$_2$CH$_3$)COOH, 3H).

RP LC/MS: $t_R$=4.59 min, m/e 579 (M+1), 533 (M−45).

TABLE 1
Compounds Where R3 is Benzisoxazole
| | MOLSTRUCTURE | PARENT WEIGHT | Mass Spec | Retention Time |
|---|---|---|---|---|
| 1 | 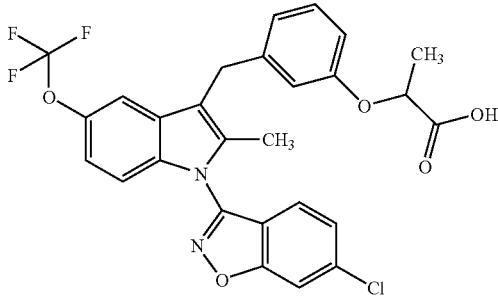 | 544.919 | 545 | 4.61 |
| 2 | 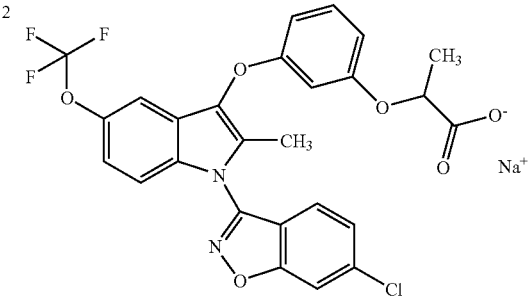 | 546.891 | 547 | 4.59 |
| 3 | 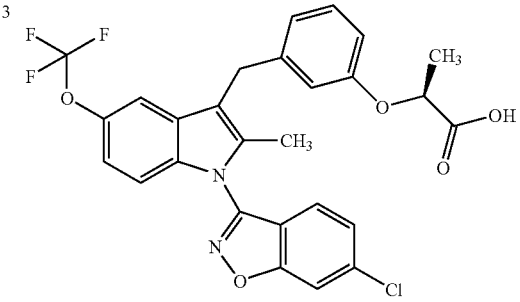 | 544.919 | 545 | 4.6 |
| 4 | 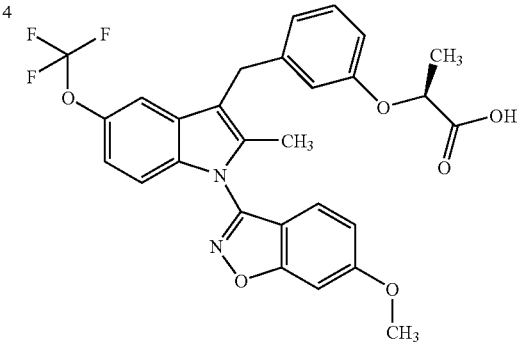 | 540.501 | 541 | 4.2 |

TABLE 1-continued
Compounds Where R3 is Benzisoxazole
| MOLSTRUCTURE | PARENT WEIGHT | Mass Spec | Retention Time |
|---|---|---|---|
| 5 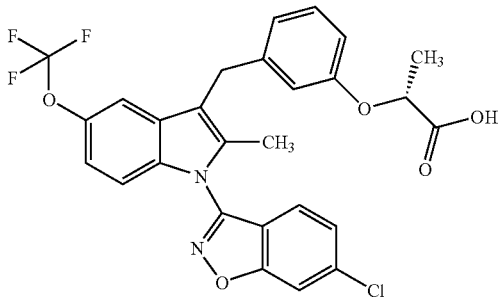 | 544.919 | 545 | 4.42 |
| 6 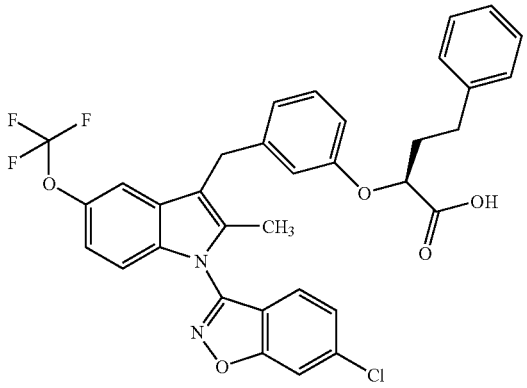 | 635.045 | 635 | 4.84 |
| 7 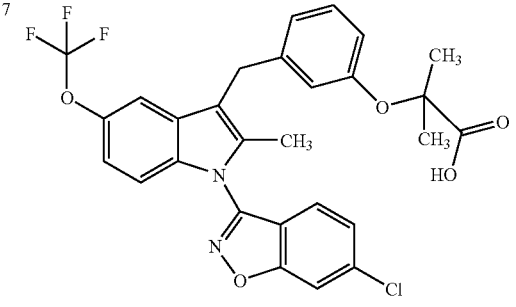 | 558.946 | 539 | 4.61 |
| 8 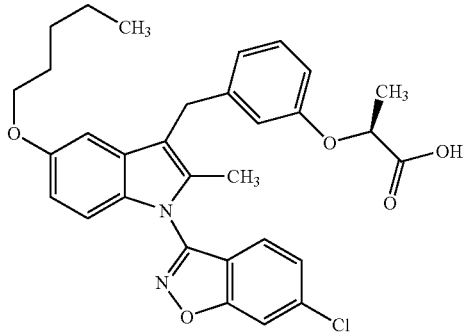 | 547.056 | 547 | 4.89 |

TABLE 1-continued

Compounds Where R3 is Benzisoxazole

| MOLSTRUCTURE | | PARENT WEIGHT | Mass Spec | Retention Time |
|---|---|---|---|---|
| 9 | | 530.892 | 531 (M + 1) | 4.02 |
| 10 | | 628.917 | 629 (M + 1) | 4.08 |
| 11 | | 546.891 | 547 | 4.46 |
| 12 | | 546.891 | 547 | 4.46 |

TABLE 1-continued

Compounds Where R3 is Benzisoxazole

| MOLSTRUCTURE | PARENT WEIGHT | Mass Spec | Retention Time |
|---|---|---|---|
| 13 | 558.946 | 559 | 4.34 |
| 14 | 574.946 | | |
| 15 | 640.981 | | |
| 16 | 570.957 | | |

TABLE 1-continued

Compounds Where R3 is Benzisoxazole

| MOLSTRUCTURE | PARENT WEIGHT | Mass Spec | Retention Time |
|---|---|---|---|
| 17 | 572.973 | | |
| 18 | 626.945 | | |
| 19 | 528.92 | | |

TABLE 1-continued
Compounds Where R3 is Benzisoxazole
| MOLSTRUCTURE | PARENT WEIGHT | Mass Spec | Retention Time |
|---|---|---|---|
| 20 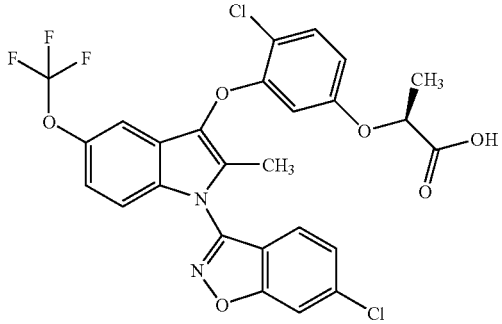 | 581.336 | 581 | 4.62 |
| 21 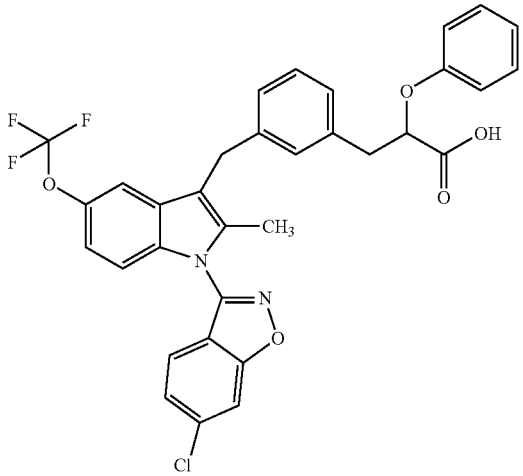 | 621.018 | | |
| 22 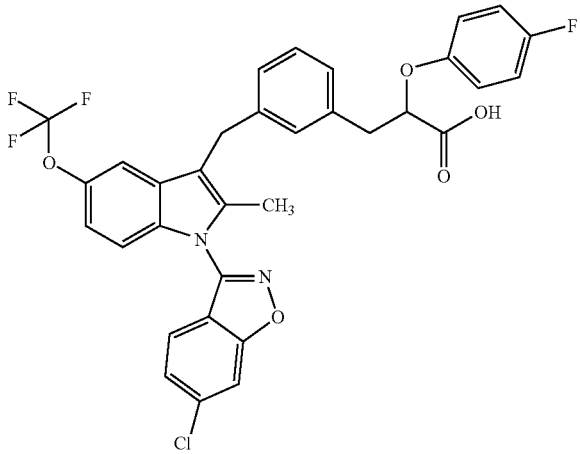 | 639.008 | | |

TABLE 1-continued
Compounds Where R3 is Benzisoxazole
| | MOLSTRUCTURE | PARENT WEIGHT | Mass Spec | Retention Time |
|---|---|---|---|---|
| 23 | 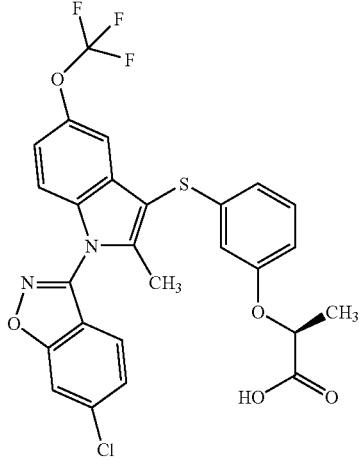 | 562.956 | 563 | 4.6 |
| 24 | 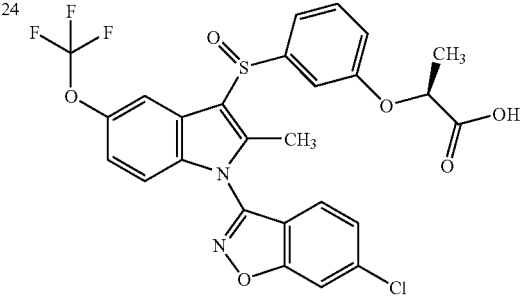 | 578.955 | 579 | 3.72 |
| 25 | 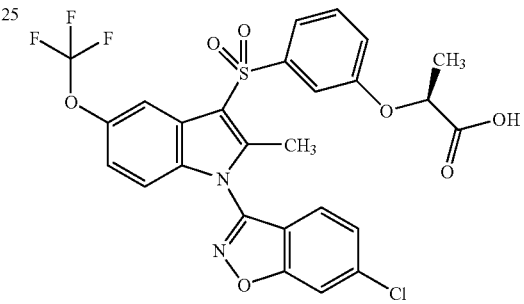 | 594.955 | 595 | 4.08 |
| 26 | 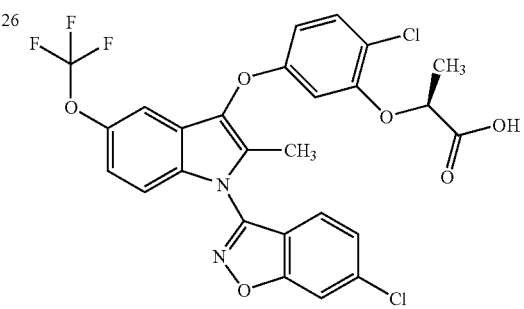 | 581.336 | 581 | 4.61 |

TABLE 1-continued
Compounds Where R3 is Benzisoxazole
| MOLSTRUCTURE | PARENT WEIGHT | Mass Spec | Retention Time |
|---|---|---|---|
| 27 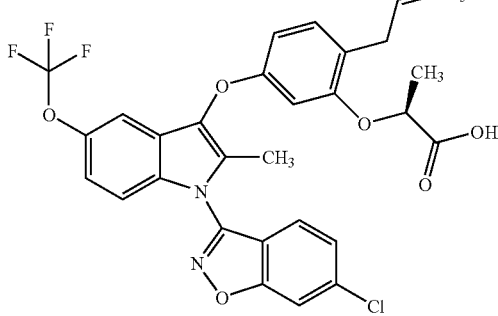 | 586.957 | 587 | 4.8 |
| 28 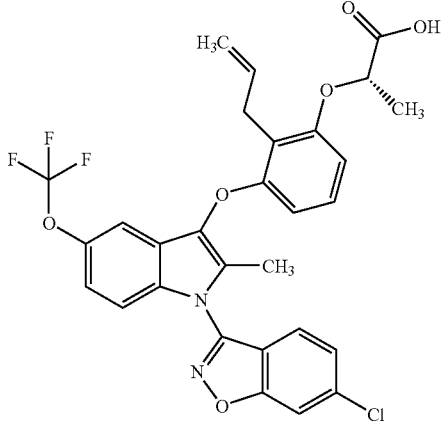 | 586.957 | 587 | 4.83 |
| 29 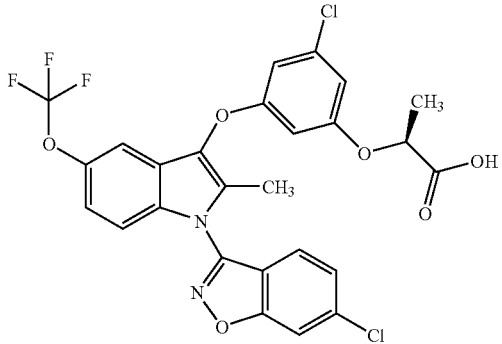 | 581.336 | 581 | 4.65 |

TABLE 1-continued
Compounds Where R3 is Benzisoxazole
| MOLSTRUCTURE | PARENT WEIGHT | Mass Spec | Retention Time |
|---|---|---|---|
| 30 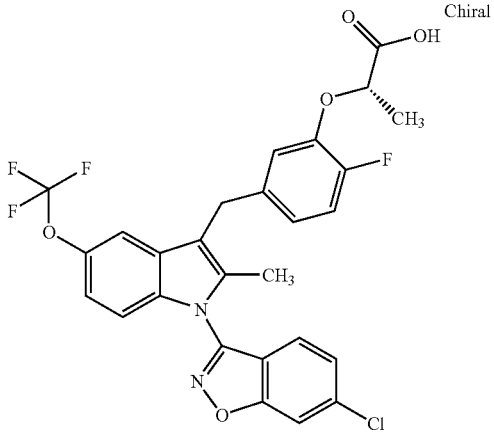 | 562.909 | 563.1 (M + 1) | 4.44 min |
| 31 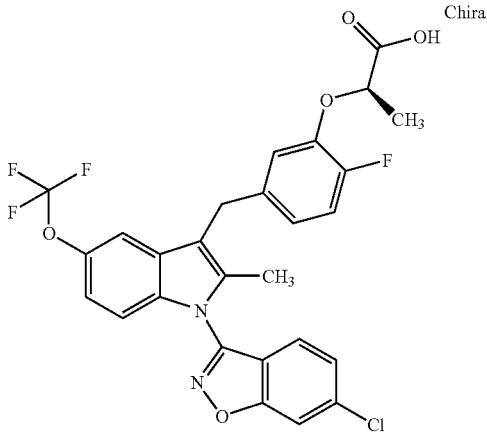 | 562.909 | 563.1 (M + 1) | 4.44 min |
| 32 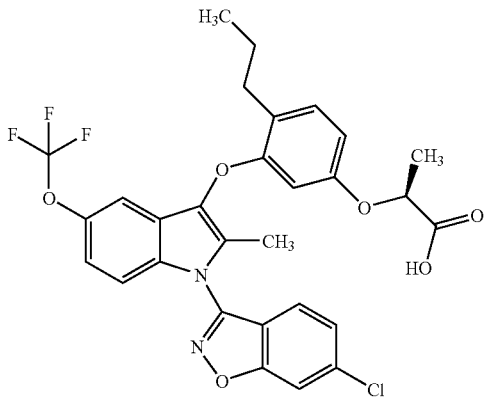 | 588.973 | 589 | 4.85 |

TABLE 1-continued
Compounds Where R3 is Benzisoxazole
| MOLSTRUCTURE | PARENT WEIGHT | Mass Spec | Retention Time |
|---|---|---|---|
| 33 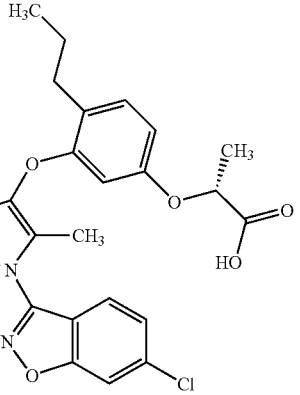 | 588.973 | 589 | 4.85 |
| 34 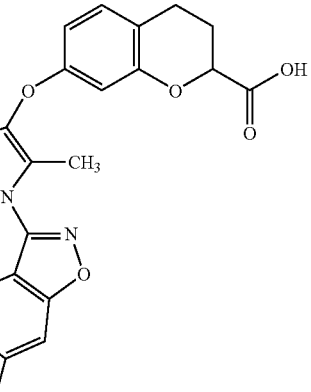 | 558.903 | | |
| 35 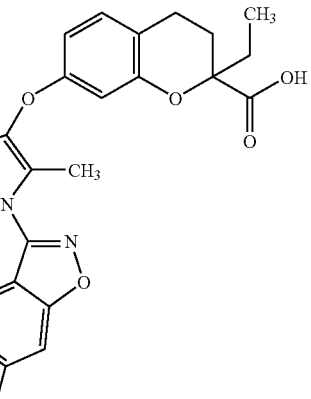 | 586.957 | M + 1 | 4.59 |
| 36 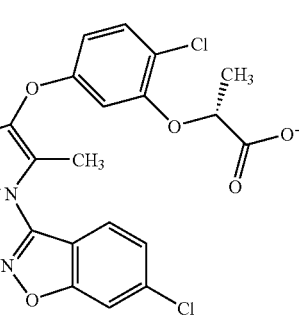 | 581.336 | 581 | 4.61 |

TABLE 1-continued

Compounds Where R3 is Benzisoxazole

| MOLSTRUCTURE | PARENT WEIGHT | Mass Spec | Retention Time |
|---|---|---|---|
| 37 | 548.929 | 549 | 4.65 |
| 38 | 576.983 | 577 | 4.71 |
| 39 | 576.983 | 577 | 4.71 |
| 40 (Chiral) | 562.909 | 563.1 (M + 1) | 4.47 min |

TABLE 1-continued
Compounds Where R3 is Benzisoxazole
| MOLSTRUCTURE | | PARENT WEIGHT | Mass Spec | Retention Time |
|---|---|---|---|---|
| 41 | 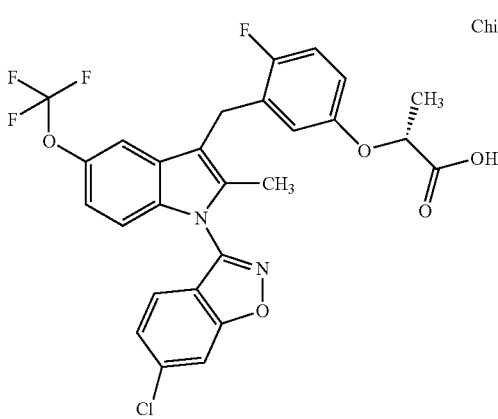 Chiral | 562.909 | 563.1 (M + 1) | 4.47 min |
| 42 | 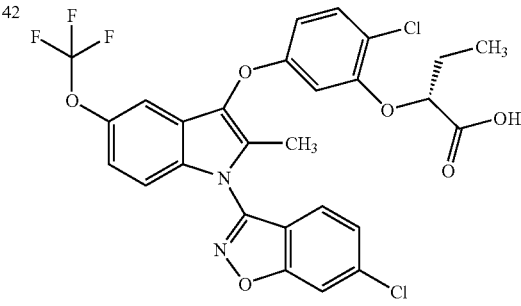 | 595.363 | 595 | 4.71 |
| 43 | 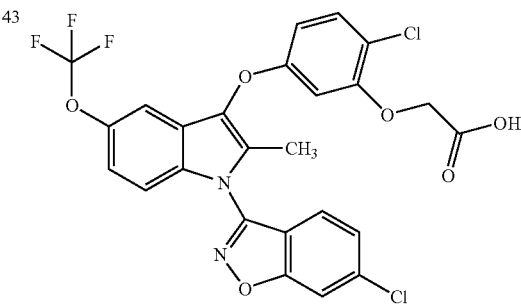 | 567.309 | 567 | 4.44 |
| 44 | 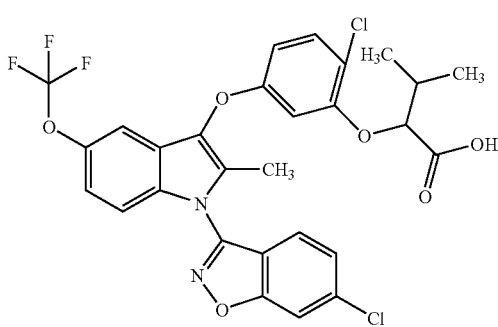 | 609.391 | 609 | 4.99 |

TABLE 1-continued
Compounds Where R3 is Benzisoxazole
| MOLSTRUCTURE | PARENT WEIGHT | Mass Spec | Retention Time |
|---|---|---|---|
| 45 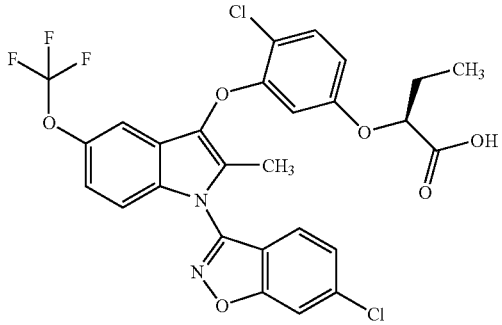 | 595.363 | 595 | 4.75 |
| 46 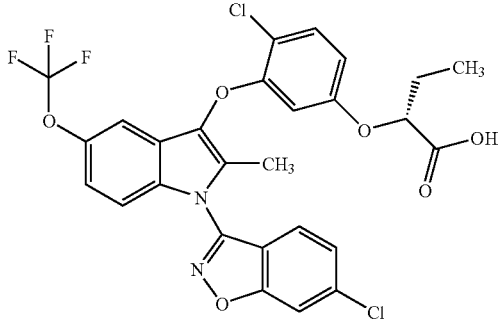 | 595.363 | 595 | 4.75 |
| 47 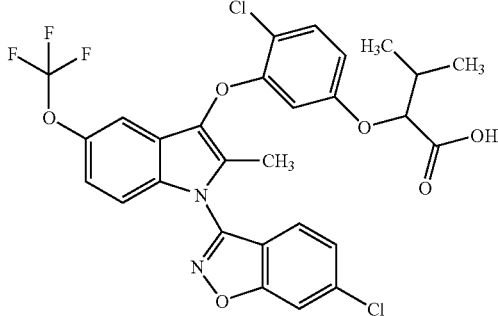 | 609.391 | 609 | 4.95 |
| 48 Chiral 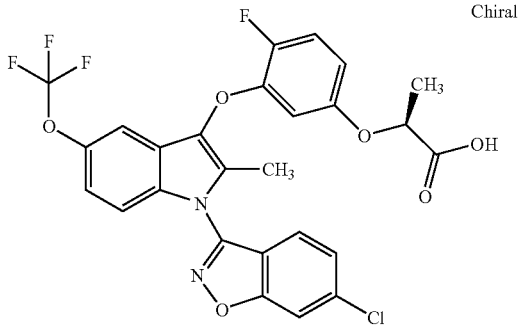 | 564.882 | 565.1 (M + 1) | 4.40 min |

TABLE 1-continued
Compounds Where R3 is Benzisoxazole
| MOLSTRUCTURE | | PARENT WEIGHT | Mass Spec | Retention Time |
|---|---|---|---|---|
| 49 | 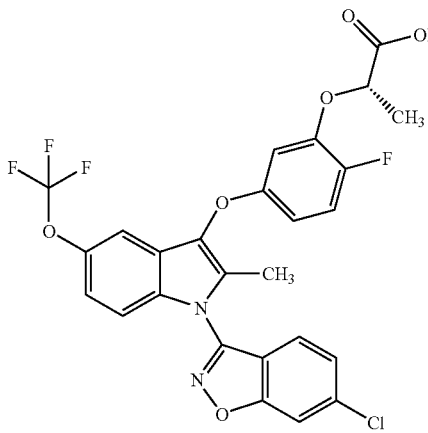 Chiral | 564.882 | 565.0 (M + 1) | 4.38 min |
| 50 | 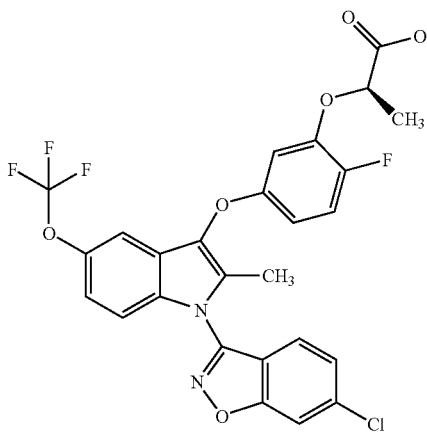 Chiral | 564.882 | 565.0 (M + 1) | 4.38 min |
| 51 | 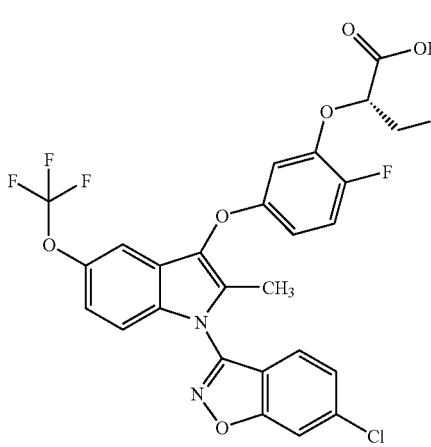 Chiral | 578.909 | 579.1 (M + 1) | 4.51 min |

TABLE 1-continued
Compounds Where R3 is Benzisoxazole
| MOLSTRUCTURE | | PARENT WEIGHT | Mass Spec | Retention Time |
|---|---|---|---|---|
| 52 | 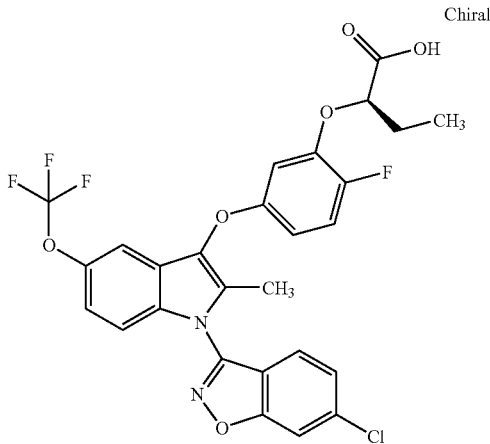 Chiral | 578.909 | 579.1 (M + 1) | 4.51 min |
| 53 | 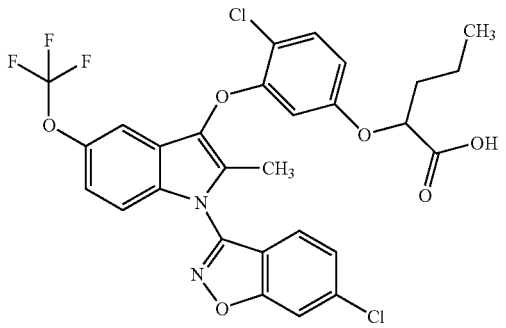 | 609.391 | 609 | 4.87 |
| 54 | 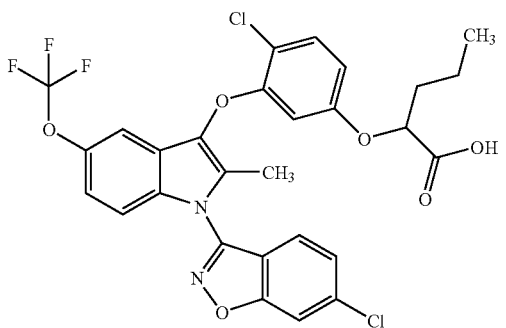 | 609.391 | 609 | 4.87 |
| 55 | 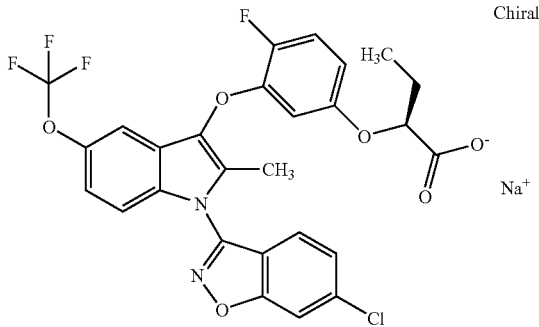 Chiral | 578.909 | 579.1 (M + 1) | 4.58 min |

TABLE 1-continued

Compounds Where R3 is Benzisoxazole

| MOLSTRUCTURE | | PARENT WEIGHT | Mass Spec | Retention Time |
|---|---|---|---|---|
| 56 | Chiral | 576.918 | 577.4 (M + H) | 4.04 min |
| 57 | | 574.49 | 575.4 (M + H) | 4.01 min |

TABLE 1A

Compounds Where R3 is Benzisoxazole 1. 2-(3-{[1-(6-chloro-1,2-benzisoxazol-3-yl)-2-methyl-5-(trifluoromethoxy)-1H-indol-3-yl]methyl}phenoxy)propanoic acid
2. 2-(3-{[1-(6-chloro-1,2-benzisoxazol-3-yl)-2-methyl-5-(trifluoromethoxy)-1H-indol-3-yl]oxy}phenoxy)propanoic acid
3. (2S)-2-(3-{[1-(6-chloro-1,2-benzisoxazol-3-yl)-2-methyl-5-(trifluoromethoxy)-1H-indol-3-yl]methyl}phenoxy)propanoic acid
4. (2S)-2-(3-{[1-(6-methoxy-1,2-benzisoxazol-3-yl)-2-methyl-5-(trifluoromethoxy)-1H-indol-3-yl]methyl}phenoxy)propanoic acid
5. (2R)-2-(3-{[1-(6-chloro-1,2-benzisoxazol-3-yl)-2-methyl-5-(trifluoromethoxy)-1H-indol-3-yl]methyl}phenoxy)propanoic acid
6. (2S)-2-(3-{[1-(6-chloro-1,2-benzisoxazol-3-yl)-2-methyl-5-(trifluoromethoxy)-1H-indol-3-yl]methyl}phenoxy)-4-phenylbutanoic acid
7. 2-(3-{[1-(6-chloro-1,2-benzisoxazol-3-yl)-2-methyl-5-(trifluoromethoxy)-1H-indol-3-yl]methyl}phenoxy)-2-methylpropanoic acid
8. (2S)-2-(3-{[1-(6-chloro-1,2-benzisoxazol-3-yl)-2-methyl-5-(pentyloxy)-1H-indol-3-yl]methyl}phenoxy)propanoic acid
9. 3-(3-{[1-(6-chloro-1,2-benzisoxazol-3-yl)-2-methyl-5-(trifluoromethoxy)-1H-indol-3-yl]oxy}phenyl)propanoic acid
10. 3-(3-{[1-(6-chloro-1,2-benzisoxazol-3-yl)-2-methyl-5-(trifluoromethoxy)-1H-indol-3-yl]oxy}phenyl)-2-(2,2,2-trifluoroethoxy)propanoic acid
11. (2S)-2-(3-{[1-(6-chloro-1,2-benzisoxazol-3-yl)-2-methyl-5-(trifluoromethoxy)-1H-indol-3-yl]oxy}phenoxy)propanoic acid
12. (2R)-2-(3-{[11-(6-chloro-1,2-benzisoxazol-3-yl)-2-methyl-5-(trifluoromethoxy)-1H-indol-3-yl]oxy}phenoxy)propanoic acid
13. (2S)-2-(3-{[1-(6-chloro-1,2-benzisoxazol-3-yl)-2-methyl-5-(2,2,2-trifluoroethoxy)-1H-indol-3-yl]methyl}phenoxy)propanoic acid
14. 3-(3-{[1-(6-chloro-1,2-benzisoxazol-3-yl)-2-methyl-5-(trifluoromethoxy)-1H-indol-3-yl]oxy}phenyl)-2-ethoxypropanoic acid
15. 3-(3-{[1-(6-chloro-1,2-benzisoxazol-3-yl)-2-methyl-5-(trifluoromethoxy)-1H-indol-3-yl]oxy}phenyl)-2-(4-fluorophenoxy)propanoic acid
16. (2S)-2-(3-{1-[1-(6-chloro-1,2-benzisoxazol-3-yl)-2-methyl-5-(trifluoromethoxy)-1H-indol-3-yl]cyclopropyl}phenoxy)propanoic acid
17. 3-(3-{[1-(6-chloro-1,2-benzisoxazol-3-yl)-2-methyl-5-(trifluoromethoxy)-1H-indol-3-yl]methyl}phenyl)-2-ethoxypropanoic acid TABLE 1A-continued Compounds Where R3 is Benzisoxazole 18  3-(3-{[1-(6-chloro-1,2-benzisoxazol-3-yl)-2-methyl-5-(trifluoromethoxy)-1H-indol-3-yl]methyl}phenyl)-2-(2,2,2-trifluoroethoxy)propanoic acid
19  3-(3-{[1-(6-chloro-1,2-benzisoxazol-3-yl)-2-methyl-5-(trifluoromethoxy)-1H-indol-3-yl]methyl}phenyl)propanoic acid
20  (2S)-2-(4-chloro-3-{[1-(6-chloro-1,2-benzisoxazol-3-yl)-2-methyl-5-(trifluoromethoxy)-1H-indol-3-yl]oxy}phenoxy)propanoic acid
21  3-(3-{[1-(6-chloro-1,2-benzisoxazol-3-yl)-2-methyl-5-(trifluoromethoxy)-1H-indol-3-yl]methyl}phenyl)-2-phenoxypropanoic acid
22  3-(3-{[1-(6-chloro-1,2-benzisoxazol-3-yl)-2-methyl-5-(trifluoromethoxy)-1H-indol-3-yl]methyl}phenyl)-2-(4-fluorophenoxy)propanoic acid
23  (2S)-2-(3-{[1-(6-chloro-1,2-benzisoxazol-3-yl)-2-methyl-5-(trifluoromethoxy)-1H-indol-3-yl]thio}phenoxy)propanoic acid
24  (2S)-2-(3-{[1-(6-chloro-1,2-benzisoxazol-3-yl)-2-methyl-5-(trifluoromethoxy)-1H-indol-3-yl]sulfinyl}phenoxy)propanoic acid
25  (2S)-2-(3-{[1-(6-chloro-1,2-benzisoxazol-3-yl)-2-methyl-5-(trifluoromethoxy)-1H-indol-3-yl]sulfonyl}phenoxy)propanoic acid
26  (2S)-2-(2-chloro-5-{[1-(6-chloro-1,2-benzisoxazol-3-yl)-2-methyl-5-(trifluoromethoxy)-1H-indol-3-yl]oxy}phenoxy)propanoic acid
27  (2S)-2-(2-allyl-5-{[1-(6-chloro-1,2-benzisoxazol-3-yl)-2-methyl-5-(trifluoromethoxy)-1H-indol-3-yl]oxy}phenoxy)propanoic acid
28  (2S)-2-(2-allyl-3-{[1-(6-chloro-1,2-benzisoxazol-3-yl)-2-methyl-5-(trifluoromethoxy)-1H-indol-3-yl]oxy}phenoxy)propanoic acid
29  (2S)-2-(3-chloro-5-{[1-(6-chloro-1,2-benzisoxazol-3-yl)-2-methyl-5-(trifluoromethoxy)-1H-indol-3-yl]oxy}phenoxy)propanoic acid
30  (2S)-2-(5-{[1-(6-chloro-1,2-benzisoxazol-3-yl)-2-methyl-5-(trifluoromethoxy)-1H-indol-3-yl]methyl}-2-fluorophenoxy)propanoic acid
31  (2R)-2-(5-{[1-(6-chloro-1,2-benzisoxazol-3-yl)-2-methyl-5-(trifluoromethoxy)-1H-indol-3-yl]methyl}-2-fluorophenoxy)propanoic acid
32  (2S)-2-(3-{[1-(6-chloro-1,2-benzisoxazol-3-yl)-2-methyl-5-(trifluoromethoxy)-1H-indol-3-yl]oxy}-4-propylphenoxy)propanoic acid
33  (2R)-2-(3-{[1-(6-chloro-1,2-benzisoxazol-3-yl)-2-methyl-5-(trifluoromethoxy)-1H-indol-3-yl]oxy}-4-propylphenoxy)propanoic acid
34  7-{[1-(6-chloro-1,2-benzisoxazol-3-yl)-2-methyl-5-(trifluoromethoxy)-1H-indol-3-yl]oxy}chromane-2-carboxylic acid
35  7-{[1-(6-chloro-1,2-benzisoxazol-3-yl)-2-methyl-5-(trifluoromethoxy)-1H-indol-3-yl]oxy}-2-ethylchromane-2-carboxylic acid
36  (2R)-2-(2-chloro-5-{[1-(6-chloro-1,2-benzisoxazol-3-yl)-2-methyl-5-(trifluoromethoxy)-1H-indol-3-yl]oxy}phenoxy)propanoic acid
37  (3-{[1-(6-chloro-1,2-benzisoxazol-3-yl)-2-methyl-5-(trifluoromethoxy)-1H-indol-3-yl]thio}phenoxy)acetic acid
38  (2S)-2-(3-{[1-(6-chloro-1,2-benzisoxazol-3-yl)-2-methyl-5-(trifluoromethoxy)-1H-indol-3-yl]thio}phenoxy)butanoic acid
39  (2R)-2-(3-{[1-(6-chloro-1,2-benzisoxazol-3-yl)-2-methyl-5-(trifluoromethoxy)-1H-indol-3-yl]thio}phenoxy)butanoic acid
40  (2S)-2-(3-{[1-(6-chloro-1,2-benzisoxazol-3-yl)-2-methyl-5-(trifluoromethoxy)-1H-indol-3-yl]methyl}-4-fluorophenoxy)propanoic acid
41  (2R)-2-(3-{[1-(6-chloro-1,2-benzisoxazol-3-yl)-2-methyl-5-(trifluoromethoxy)-1H-indol-3-yl]methyl}-4-fluorophenoxy)propanoic acid
42  (2R)-2-(2-chloro-5-{[1-(6-chloro-1,2-benzisoxazol-3-yl)-2-methyl-5-(trifluoromethoxy)-1H-indol-3-yl]oxy}phenoxy)butanoic acid
43  (2-chloro-5-{[1-(6-chloro-1,2-benzisoxazol-3-yl)-2-methyl-5-(trifluoromethoxy)-1H-indol-3-yl]oxy}phenoxy)acetic acid
44  2-(2-chloro-5-{[1-(6-chloro-1,2-benzisoxazol-3-yl)-2-methyl-5-(trifluoromethoxy)-1H-indol-3-yl]oxy}phenoxy)-3-methylbutanoic acid
45  (2S)-2-(4-chloro-3-{[1-(6-chloro-1,2-benzisoxazol-3-yl)-2-methyl-5-(trifluoromethoxy)-1H-indol-3-yl]oxy}phenoxy)butanoic acid
46  (2R)-2-(4-chloro-3-{[1-(6-chloro-1,2-benzisoxazol-3-yl)-2-methyl-5-(trifluoromethoxy)-1H-indol-3-yl]oxy}phenoxy)butanoic acid
47  2-(4-chloro-3-{[1-(6-chloro-1,2-benzisoxazol-3-yl)-2-methyl-5-(trifluoromethoxy)-1H-indol-3-yl]oxy}phenoxy)-3-methylbutanoic acid
48  (2S)-2-(3-{[1-(6-chloro-1,2-benzisoxazol-3-yl)-2-methyl-5-(trifluoromethoxy)-1H-indol-3-yl]oxy}-4-fluorophenoxy)propanoic acid
49  (2S)-2-(5-{[1-(6-chloro-1,2-benzisoxazol-3-yl)-2-methyl-5-(trifluoromethoxy)-1H-indol-3-yl]oxy}-2-fluorophenoxy)propanoic acid
50  (2R)-2-(5-{[1-(6-chloro-1,2-benzisoxazol-3-yl)-2-methyl-5-(trifluoromethoxy)-1H-indol-3-yl]oxy}-2-fluorophenoxy)propanoic acid
51  (2S)-2-(5-{[1-(6-chloro-1,2-benzisoxazol-3-yl)-2-methyl-5-(trifluoromethoxy)-1H-indol-3-yl]oxy}-2-fluorophenoxy)butanoic acid
52  (2R)-2-(5-{[1-(6-chloro-1,2-benzisoxazol-3-yl)-2-methyl-5-(trifluoromethoxy)-1H-indol-3-yl]oxy}-2-fluorophenoxy)butanoic acid
53  2-(4-chloro-3-{[1-(6-chloro-1,2-benzisoxazol-3-yl)-2-methyl-5-(trifluoromethoxy)-1H-indol-3-yl]oxy}phenoxy)pentanoic acid
54  2-(4-chloro-3-{[1-(6-chloro-1,2-benzisoxazol-3-yl)-2-methyl-5-(trifluoromethoxy)-1H-indol-3-yl]oxy}phenoxy)pentanoic acid
55  (2S)-2-(3-{[1-(6-chloro-1,2-benzisoxazol-3-yl)-2-methyl-5-(trifluoromethoxy)-1H-indol-3-yl]oxy}-4-fluorophenoxy)butanoic acid TABLE 1A-continued Compounds Where R3 is Benzisoxazole 56 (2S)-2-(4-chloro-3-{[1-(6-methoxy-1,2-benzisoxazol-3-yl)-2-methyl-5-(trifluoromethoxy)-1H-indol-3-yl]oxy}phenoxy)propanoic acid
57 (2S)-2-(4-fluoro-3-{[1-(6-methoxy-1,2-benzisoxazol-3-yl)-2-methyl-5-(trifluoromethoxy)-1H-indol-3-yl]oxy}phenoxy)butanoic acid

What is claimed is:

1. A compound of formula I:

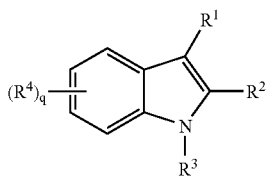

or a pharmaceutically acceptable salt thereof, wherein:

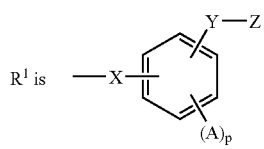

wherein X is selected from the group consisting of a bond, O, $S(O)_n$, $CH_2$, and $C_{3-6}$cycloalkylidene;
Y is selected from the group consisting of —$OCR^7R^8$—, and —$CH_2CR^5R^6$—;
Z is selected from the group consisting of —$CO_2H$ and tetrazole;
A is selected from the group consisting of H, $C_{1-4}$alkyl, $C_{1-4}$ alkenyl, —$OC_{1-4}$ alkyl, and halogen, wherein alkyl, alkenyl, and Oalkyl are optionally substituted with 1-5 halogens;
$R^5, R^6, R^7$, and $R^8$ are each independently selected from the group consisting of H, halogen, $C_1$-$C_5$ alkyl, $OC_1$-$C_5$ alkyl, $C_2$-$C_5$ alkenyl, $C_2$-$C_5$ alkenyl, $C_{3-6}$ cycloalkyl, $(CH_2)_{0-2}$phenyl, —$O(CH_2)_{0-2}$phenyl and $CO_2H$, wherein $C_1$-$C_5$ alkyl, $OC_1$-$C_5$ alkyl, $C_2$-$C_5$ alkenyl, $OC_2$-$C_5$ alkenyl, $C_{3-6}$ cycloalkyl, and phenyl are optionally substituted with 1-5 halogens, and $C_{3-6}$ cycloalkyl and phenyl are further optionally substituted with 1-3 groups independently selected from $C_1$-$C_3$ alkyl and $OC_1$-$C_3$ alkyl, said $C_1$-$C_3$ alkyl and $OC_1$-$C_3$ alkyl being optionally substituted with 1-3 halogens;
$R^2$ is $C_1$-$C_4$ alkyl, which is optionally substituted with 1-5 halogens;
$R^3$ is 3-benzisoxazolyl optionally substituted with 1-3 groups independently selected from halogen, $C_{1-3}$alkyl, and $OC_{1-3}$alkyl, wherein $C_{1-3}$alkyl and $OC_{1-3}$alkyl are optionally substituted with 1-5 halogens;
each $R^4$ is independently selected from the group consisting of halogen, $C_1$-$C_3$ alkyl, and $OC_1$-$C_5$ alkyl, wherein $C_1$-$C_3$ alkyl and $OC_1$-$C_5$ alkyl are optionally substituted with 1-5 halogens;
n is an integer from 0-2;
p is an integer from 0-3; and
q is an integer from 0-3.

2. A compound according to claim 1, wherein q is an integer from 1-3.

3. A compound according to claim 1, wherein
X is selected from the group consisting of a bond, O, $S(O)_n$, $CH_2$, and $C_{3-6}$cycloalkylidene;
Y is selected from the group consisting of $OCR^7R^8$ and $CH_2CR^5R^6$;
Z is selected from $CO_2H$ and tetrazole;
A is selected from the group consisting of H, $CH_3$, $CF_3$, $OCH_3$, $OCF_3$, and halogen;
$R^5$, $R^6$, and $R^7$ are each independently selected from the group consisting of H, halogen, $C_1$-$C_3$ alkyl, and $OC_1$-$C_3$ alkyl, and $R^8$ is selected from the group consisting of halogen, $C_1$-$C_3$ alkyl, and $OC_1$-$C_3$ alkyl, wherein $C_1$-$C_3$ alkyl and $OC_1$-$C_3$ alkyl of $R^5$, $R^6$, $R^7$, and $R^8$ are optionally substituted with 1-3 halogens;
$R^2$ is $C_1$-$C_3$alkyl;
$R^3$ is benzisoxazolyl optionally substituted with 1-3 groups independently selected from halogen, $OCH_3$, $OCF_3$, $CH_3$, and $CF_3$;
each group $R^4$ is selected from $OCH_3$, $OCF_3$, and $CF_3$; and
p is 1.

4. A compound according to claim 3, wherein $R^5$, $R^6$, and $R^7$ are each independently selected from the group consisting of H, halogen, $C_1$-$C_3$ alkyl, and $OC_1$-$C_3$ alkyl, and $R^8$ is selected from the group consisting of halogen, $C_1$-$C_3$ alkyl, and $OC_1$-$C_3$ alkyl; and q is an integer from 1-3.

5. A compound according to claim 3, wherein
X is selected from the group consisting of O, $S(O)_n$, and $CH_2$;
Y is selected from the group consisting of $OCR^7R^8$ and $CH_2CR^5R^6$;
Z is $CO_2H$;
A is selected from the group consisting of H, $CH_3$, $CF_3$, $OCH_3$, $OCF_3$, and halogen;
$R^5$ is H;
$R^6$ is selected from H and $OC_1$-$C_3$ alkyl, which is optionally substituted with 1-3 halogens;
$R^7$ is selected froni the group consisting of H and $C_1$-$C_3$ alkyl;
$R^8$ is $C_1$-$C_3$ alkyl;
$R^2$ is $C_1$-$C_3$ alkyl; and
$R^3$ is benzisoxazolyl optionally substituted with 1 group independently selected from halogen, $OCH_3$, $OCF_3$, $CH_3$, and $CF_3$.

6. A compound according to claim 5, wherein q is 1.

7. A compound according to claim 2, wherein Y is $OCR^7R^8$; $R^7$ is selected from the group consisting of H and $C_1$-$C_3$ alkyl; and $R^8$ is $C_1$-$C_3$ alkyl.

8. A compound according to claim 2, wherein $R^2$ is $CH_3$.

9. A compound according to claim 2, wherein Z is $CO_2H$.

10. A compound according to claim 2, wherein $R^3$ is 3-benzisoxazolyl, which is optionally substituted with 1-3 substituents independently selected from halogen, $OCH_3$, $OCF_3$, $CH_3$, and $CF_3$.

11. A compound according to claim 4, wherein R³ is 3-benzisoxazolyl, which is optionally substituted with 1 substituent selected from halogen, OCH₃, OCF₃, and CF₃.

12. A compound according to claim 5, wherein
X and YZ are meta to each other on the phenyl ring of R¹;
R⁴ is selected from OCH₃, OCF₃, and CF₃;
X is selected from O and CH₂;
Y is OC*R⁷R⁸, wherein R⁷ is H and R⁸ is C₁-C₃ alkyl;
R² is CH3; and R³ is 3-benzisoxazolyl, which is optionally substituted with 1 substituent selected from halogen, OCH₃, OCF₃, and CF₃.

13. A compound according to claim 12, wherein q is 1.
14. A compound according to claim 13, wherein the asymmetric C* carbon of Y has the R configuration.
15. A compound according to claim 13, wherein the asymmetric C* carbon of Y has the S configuration.
16. A compound according to claim 1 as named below, or a pharmaceutically acceptable salt thereof:

1  2-(3-{[1-(6-chloro-1,2-benzisoxazol-3-yl)-2-methyl-5-(trifluoromethoxy)-1H-indol-3-yl]methyl}phenoxy)propanoic acid
2  2-(3-{[1-(6-chloro-1,2-benzisoxazol-3-yl)-2-methyl-5-(trifluoromethoxy)-1H-indol-3-yl]oxy}phenoxy)propanoic acid
3  (2S)-2-(3-{[1-(6-chloro-1,2-benzisoxazol-3-yl)-2-methyl-5-(trifluoromethoxy)-1H-indol-3-yl]methyl}phenoxy)propanoic acid
4  (2S)-2-(3-{[1-(6-methoxy-1,2-benzisoxazol-3-yl)-2-methyl-5-(trifluoromethoxy)-1H-indol-3-yl]methyl}phenoxy)propanoic acid
5  (2R)-2-(3-{[1-(6-chloro-1,2-benzisoxazol-3-yl)-2-methyl-5-(trifluoromethoxy)-1H-indol-3-yl]methyl}phenoxy)propanoic acid
6  (2S)-2-(3-{[1-(6-chloro-1,2-benzisoxazol-3-yl)-2-methyl-5-(trifluoromethoxy)-1H-indol-3-yl]methyl}phenoxy)-4-phenylbutanoic acid
7  2-(3-{[1-(6-chloro-1,2-benzisoxazol-3-yl)-2-methyl-5-(trifluoromethoxy)-1H-indol-3-yl]methyl}phenoxy)-2-methylpropanoic acid
8  (2S)-2-(3-{[1-(6-chloro-1,2-benzisoxazol-3-yl)-2-methyl-5-(pentyloxy)-1H-indol-3-yl]methyl}phenoxy)propanoic acid
9  3-(3-{[1-(6-chloro-1,2-benzisoxazol-3-yl)-2-methyl-5-(trifluoromethoxy)-1H-indol-3-yl]oxy}phenyl)propanoic acid
10  3-(3-{[1-(6-chloro-1,2-benzisoxazol-3-yl)-2-methyl-5-(trifluoromethoxy)-1H-indol-3-yl]oxy}phenyl)-2-(2,2,2-trifluoroethoxy)propanoic acid
11  (2S)-2-(3-{[1-(6-chloro-1,2-benzisoxazol-3-yl)-2-methyl-5-(trifluoromethoxy)-1H-indol-3-yl]oxy}phenoxy)propanoic acid
12  (2R)-2-(3-{[1-(6-chloro-1,2-benzisoxazol-3-yl)-2-methyl-5-(trifluoromethoxy)-1H-indol-3-yl]oxy}phenoxy)propanoic acid
13  (2S)-2-(3-{[1-(6-chloro-1,2-benzisoxazol-3-yl)-2-methyl-5-(2,2,2-trifluoroethoxy)-1H-indol-3-yl]methyl}phenoxy)propanoic acid
14  3-(3-{[1-(6-chloro-1,2-benzisoxazol-3-yl)-2-methyl-5-(trifluoromethoxy)-1H-indol-3-yl]oxy}phenyl)-2-ethoxypropanoic acid
15  3-(3-{[1-(6-chloro-1,2-benzisoxazol-3-yl)-2-methyl-5-(trifluoromethoxy)-1H-indol-3-yl]oxy}phenyl)-2-(4-fluorophenoxy)propanoic acid
16  (2S)-2-(3-{1-[1-(6-chloro-1,2-benzisoxazol-3-yl)-2-methyl-5-(trifluoromethoxy)-1H-indol-3-yl]cyclopropyl}phenoxy)propanoic acid
17  3-(3-{[1-(6-chloro-1,2-benzisoxazol-3-yl)-2-methyl-5-(trifluoromethoxy)-1H-indol-3-yl]methyl}phenyl)-2-ethoxypropanoic acid
18  3-(3-{[1-(6-chloro-1,2-benzisoxazol-3-yl)-2-methyl-5-(trifluoromethoxy)-1H-indol-3-yl]methyl}phenyl)-2-(2,2,2-trifluoroethoxy)propanoic acid
19  3-(3-{[1-(6-chloro-1,2-benzisoxazol-3-yl)-2-methyl-5-(trifluoromethoxy)-1H-indol-3-yl]methyl}phenyl)propanoic acid
20  (2S)-2-(4-chloro-3-{[1-(6-chloro-1,2-benzisoxazol-3-yl)-2-methyl-5-(trifluoromethoxy)-1H-indol-3-yl]oxy}phenoxy)propanoic acid
21  3-(3-{[1-(6-chloro-1,2-benzisoxazol-3-yl)-2-methyl-5-(trifluoromethoxy)-1H-indol-3-yl]methyl}phenyl)-2-phenoxypropanoic acid
22  3-(3-{[1-(6-chloro-1,2-benzisoxazol-3-yl)-2-methyl-5-(trifluoromethoxy)-1H-indol-3-yl]methyl}phenyl)-2-(4-fluorophenoxy)propanoic acid
23  (2S)-2-(3-{[1-(6-chloro-1,2-benzisoxazol-3-yl)-2-methyl-5-(trifluoromethoxy)-1H-indol-3-yl]thio}phenoxy)propanoic acid
24  (2S)-2-(3-{[1-(6-chloro-1,2-benzisoxazol-3-yl)-2-methyl-5-(trifluoromethoxy)-1H-indol-3-yl]sulfinyl}phenoxy)propanoic acid
25  (2S)-2-(3-{[1-(6-chloro-1,2-benzisoxazol-3-yl)-2-methyl-5-(trifluoromethoxy)-1H-indol-3-yl]sulfonyl}phenoxy)propanoic acid
26  (2S)-2-(2-chloro-5-{[1-(6-chloro-1,2-benzisoxazol-3-yl)-2-methyl-5-(trifluoromethoxy)-1H-indol-3-yl]oxy}phenoxy)propanoic acid
27  (2S)-2-(2-allyl-5-{[1-(6-chloro-1,2-benzisoxazol-3-yl)-2-methyl-5-(trifluoromethoxy)-1H-indol-3-yl]oxy}phenoxy)propanoic acid
28  (2S)-2-(2-allyl-3-{[1-(6-chloro-1,2-benzisoxazol-3-yl)-2-methyl-5-(trifluoromethoxy)-1H-indol-3-yl]oxy}phenoxy)propanoic acid
29  (2S)-2-(3-chloro-5-{[1-(6-chloro-1,2-benzisoxazol-3-yl)-2-methyl-5-(trifluoromethoxy)-1H-indol-3-yl]oxy}phenoxy)propanoic acid
30  (2S)-2-(5-{[1-(6-chloro-1,2-benzisoxazol-3-yl)-2-methyl-5-(trifluoromethoxy)-1H-indol-3-yl]methyl}-2-fluorophenoxy)propanoic acid
31  (2R)-2-(5-{[1-(6-chloro-1,2-benzisoxazol-3-yl)-2-methyl-5-(trifluoromethoxy)-1H-indol-3-yl]methyl}-2-fluorophenoxy)propanoic acid
32  (2S)-2-(3-{[1-(6-chloro-1,2-benzisoxazol-3-yl)-2-methyl-5-(trifluoromethoxy)-1H-indol-3-yl]oxy}-4-propylphenoxy)propanoic acid

| | -continued |
|---|---|
| 33 | (2R)-2-(3-{[1-(6-chloro-1,2-benzisoxazol-3-yl)-2-methyl-5-(trifluoromethoxy)-1H-indol-3-yl]oxy}-4-propylphenoxy)propanoic acid |
| 34 | 7-{[1-(6-chloro-1,2-benzisoxazol-3-yl)-2-methyl-5-(trifluoromethoxy)-1H-indol-3-yl]oxy}chromane-2-carboxylic acid |
| 35 | 7-{[1-(6-chloro-1,2-benzisoxazol-3-yl)-2-methyl-5-(trifluoromethoxy)-1H-indol-3-yl]oxy}-2-ethylchromane-2-carboxylic acid |
| 36 | (2R)-2-(2-chloro-5-{[1-(6-chloro-1,2-benzisoxazol-3-yl)-2-methyl-5-(trifluoromethoxy)-1H-indol-3-yl]oxy}phenoxy)propanoic acid |
| 37 | (3-{[1-(6-chloro-1,2-benzisoxazol-3-yl)-2-methyl-5-(trifluoromethoxy)-1H-indol-3-yl]thio}phenoxy)acetic acid |
| 38 | (2S)-2-(3-{[1-(6-chloro-1,2-benzisoxazol-3-yl)-2-methyl-5-(trifluoromethoxy)-1H-indol-3-yl]thio}phenoxy)butanoic acid |
| 39 | (2R)-2-(3-{[1-(6-chloro-1,2-benzisoxazol-3-yl)-2-methyl-5-(trifluoromethoxy)-1H-indol-3-yl]thio}phenoxy)butanoic acid |
| 40 | (2S)-2-(3-{[1-(6-chloro-1,2-benzisoxazol-3-yl)-2-methyl-5-(trifluoromethoxy)-1H-indol-3-yl]methyl}-4-fluorophenoxy)propanoic acid |
| 41 | (2R)-2-(3-{[1-(6-chloro-1,2-benzisoxazol-3-yl)-2-methyl-5-(trifluoromethoxy)-1H-indol-3-yl]methyl}-4-fluorophenoxy)propanoic acid |
| 42 | (2R)-2-(2-chloro-5-{[1-(6-chloro-1,2-benzisoxazol-3-yl)-2-methyl-5-(trifluoromethoxy)-1H-indol-3-yl]oxy}phenoxy)butanoic acid |
| 43 | (2-chloro-5-{[1-(6-chloro-1,2-benzisoxazol-3-yl)-2-methyl-5-(trifluoromethoxy)-1H-indol-3-yl]oxy}phenoxy)acetic acid |
| 44 | 2-(2-chloro-5-{[1-(6-chloro-1,2-benzisoxazol-3-yl)-2-methyl-5-(trifluoromethoxy)-1H-indol-3-yl]oxy}phenoxy)-3-methylbutanoic acid |
| 45 | (2S)-2-(4-chloro-3-{[1-(6-chloro-1,2-benzisoxazol-3-yl)-2-methyl-5-(trifluoromethoxy)-1H-indol-3-yl]oxy}phenoxy)butanoic acid |
| 46 | (2R)-2-(4-chloro-3-{[1-(6-chloro-1,2-benzisoxazol-3-yl)-2-methyl-5-(trifluoromethoxy)-1H-indol-3-yl]oxy}phenoxy)butanoic acid |
| 47 | 2-(4-chloro-3-{[1-(6-chloro-1,2-benzisoxazol-3-yl)-2-methyl-5-(trifluoromethoxy)-1H-indol-3-yl]oxy}phenoxy)-3-methylbutanoic acid |
| 48 | (2S)-2-(3-{[1-(6-chloro-1,2-benzisoxazol-3-yl)-2-methyl-5-(trifluoromethoxy)-1H-indol-3-yl]oxy}-4-fluorophenoxy)propanoic acid |
| 49 | (2S)-2-(5-{[1-(6-chloro-1,2-benzisoxazol-3-yl)-2-methyl-5-(trifluoromethoxy)-1H-indol-3-yl]oxy}-2-fluorophenoxy)propanoic acid |
| 50 | (2R)-2-(5-{[1-(6-chloro-1,2-benzisoxazol-3-yl)-2-methyl-5-(trifluoromethoxy)-1H-indol-3-yl]oxy}-2-fluorophenoxy)propanoic acid |
| 51 | (2S)-2-(5-{[1-(6-chloro-1,2-benzisoxazol-3-yl)-2-methyl-5-(trifluoromethoxy)-1H-indol-3-yl]oxy}-2-fluorophenoxy)butanoic acid |
| 52 | (2R)-2-(5-{[1-(6-chloro-1,2-benzisoxazol-3-yl)-2-methyl-5-(trifluoromethoxy)-1H-indol-3-yl]oxy}-2-fluorophenoxy)butanoic acid |
| 53 | 2-(4-chloro-3-{[1-(6-chloro-1,2-benzisoxazol-3-yl)-2-methyl-5-(trifluoromethoxy)-1H-indol-3-yl]oxy}phenoxy)pentanoic acid |
| 54 | 2-(4-chloro-3-{[1-(6-chloro-1,2-benzisoxazol-3-yl)-2-methyl-5-(trifluoromethoxy)-1H-indol-3-yl]oxy}phenoxy)pentanoic acid |
| 55 | (2S)-2-(3-{[1-(6-chloro-1,2-benzisoxazol-3-yl)-2-methyl-5-(trifluoromethoxy)-1H-indol-3-yl]oxy}-4-fluorophenoxy)butanoic acid |
| 56 | (2S)-2-(4-chloro-3-{[1-(6-methoxy-1,2-benzisoxazol-3-yl)-2-methyl-5-(trifluoromethoxy)-1H-indol-3-yl]oxy}phenoxy)propanoic acid |
| 57 | (2S)-2-(4-fluoro-3-{[1-(6-methoxy-1,2-benzisoxazol-3-yl)-2-methyl-5-(trifluoromethoxy)-1H-indol-3-yl]oxy}phenoxy)butanoic acid |

17. A pharmaceutical composition comprising a compound of claim 1, or a pharmaceutically acceptable salt thereof, and a pharmaceutically acceptable carrier.

* * * * *